United States Patent [19]

Lieberman et al.

[11] Patent Number: 5,198,356
[45] Date of Patent: Mar. 30, 1993

[54] MONOPHENOTYPIC IN VITRO CELL LINES OF MEGAKARYOCYTIC LINEAGE, PRODUCTS PRODUCED THEREBY AND METHODS

[75] Inventors: Michael A. Lieberman; Douglas A. Fugman, both of Cincinnati, Ohio

[73] Assignees: Children's Hospital Medical Center; University of Cincinnati, Cincinnati, Ohio

[21] Appl. No.: 493,106

[22] Filed: Mar. 12, 1990

[51] Int. Cl.$^5$ .............................................. C12N 5/00
[52] U.S. Cl. .............................. 435/240.2; 435/204.1; 435/240.23
[58] Field of Search ...................... 435/2, 240.1, 240.2, 435/240.21, 240.23, 240.243, 240.3, 68, 948, 399; 530/837, 840, 838, 828

[56] References Cited

PUBLICATIONS

Fugman, "Invitroestablishment and Characterization of a Human Megakaryocytic Cell Line CHRF-288 Utilizing Long-Term Bone Marrow Cultures as a Supportive Microenvironment", Thesis, University of Cincinnati, Mar. 1988.

Wyke et al., "Perturbed Hemopoiesis And the Generation of Multipotential Stem Cell Clones in SRC-infected Bone Marrow Cultures is an Indirect or Transient Effect of the Oncogene", Molecular and Cellular Biology, Mar. 1986, 959-963.

Tetteroo et al., "Megakaryoblastic Differentiation of Proetythroblastic 1562 Cell Line Cells", Leukemia Research, V. 8 (2), 197206, 1984.

Fugman et al., "In Vitro Establishment and Characterization of a Human Megakaryoblastic Cell Line", Blood, V. 75 (6), 1252-1261, 1990.

Primary Examiner—Y. Christina Chan
Assistant Examiner—Donald E. Adams
Attorney, Agent, or Firm—Wood, Herron & Evans

[57] ABSTRACT

Human monophenotypic cloned cell lines of megakaryocytic lineage are established in vitro through use of adherent stromal cells in long term human bone marrow culture. Long term bone marrow cultures are used for initial adaptation of the cells to culture conditions. Once adapted, cells of the human in vitro cell lines are weaned from the stromal layer until they proliferate in the complete absence of any feeder layer. Seed cells for establishment of human in vitro cell lines were derived from a human solid tumor designated as ATCC CRL 9139 xenograft. Cells of one cloned in vitro cell line designated as CHRF-288-11 exhibits a karyotype and markers characteristic of megakaryocytes and platelets. Cells of the CHRF-288-11 cell line express platelet peroxidate, platelet factor IV, platelet $Ca^{++}$-ATPase, gpIIbIIIa, factor VIII, and MY7, MY9 and HLA-Dr antigens. CHRF-288-11 cell line exhibits a constant karyotype (50, XY). CHRF-288-11 cell line is deposited under the Budapest Treaty with American Type Culture Collection, 12301 Parklawn Drive, Rockville, Md. 20852, under accession No. CRL 10107.

9 Claims, 18 Drawing Sheets

| LANE | SAMPLE | PROBE |
|---|---|---|
| 1 | 10ng PURIFIED TGF-B | anti-TGF-B |
| 2 | ACID EtOH EXTRACT OF TUMOR CELLS | anti-TGF-B |
| 3 | ACID EtOH EXTRACT OF TUMOR CELLS | anti-EGF |

MONOPHENOTYPIC IN VITRO CELL LINES OF MEGAKARYOCYTIC LINEAGE, PRODUCTS PRODUCED THEREBY AND METHODS

FIELD OF THE INVENTION

The present invention relates to novel monophenotypic in vitro cell lines of megakaryocytic lineage, methods of propagating in vitro cell lines, and products generated by the in vitro cell lines.

BACKGROUND

Cell regulation is mediated by a wide variety of polypeptides. Historically, few of these polypeptides are produced in sufficient amounts to be isolated and characterized. Even in those situations where particular polypeptides are capable of isolation and characterization, the number of amino acids constituting the polypeptides normally preclude synthesis by conventional polypeptide bond formation in commercially useful amounts.

In the last few years, however, a number of discoveries relating to biotechnology have occurred which at the present time promise opportunities for the detection, isolation and production in commercially useful amounts of naturally occurring proteins, which fulfill a wide variety of cell regulatory functions.

The ability to isolate, characterize and insert a gene into a replicating vector, such as a plasmid or phage, and transform a microorganism with the resulting hybrid has introduced new techniques, i.e., genetic engineering techniques, for the production of macromolecular polypeptides. These techniques not only afford the opportunity to obtain polypeptides in abundance, but allow for study of the polypeptides and use of the polypeptides in regulating cell functions in vitro and in vivo.

Because of the cumbersome nature and difficulties associated with synthesis and existence of introns present in chromosomal DNA, the messenger RNA is frequently the desired route where genetic engineering is involved. In each cell, there is continuously produced a large number of different messenger RNA molecules. Therefore, means must be provided for isolating the messenger RNA of interest from other messenger RNA molecules. Where a messenger RNA of interest is normally produced in only small amounts as compared to the total amount of messenger RNAs, it is frequently desirable, if not necessary, to obtain cells which enhance the amount of messenger RNA of interest present in the cell.

As an alternative to genetic engineering, the ability to culture cells offers an opportunity for the production of a wide variety of polypeptides. By isolating specific cells and establishing a culture, which can be expanded and maintained for extensive periods of time, one can directly produce the polypeptides of interest from the cultured cells. In this manner, one avoids the need to isolate the gene or messenger RNA of interest and perform the numerous complicated steps involved with successful genetic engineering.

The regulation of cell growth is a poorly understood topic. A large number of growth regulatory factors have been described heretofore which can either stimulate or inhibit cell growth. A total understanding of the integration of all the signals a cell receives from these factors has not yet been achieved. While such factors have been isolated from many sources, platelets are known to contain large quantities of a variety of potent growth factors. Platelet-derived growth factor (PDGF) and the transforming growth factors alpha and beta (TGF-alpha, TGF-beta, respectively,) fall into this category. Not much is known concerning the physiological function of these factors, although roles have been postulated for both PDGF and TGF-beta in the process of arterial wall wound repair. PDGF is a very potent mitogen for smooth muscle cells, fibroblasts and glial cells. The addition of PDGF to such cells renders the cells competent to enter the cell cycle. A second set of growth factors, termed progression factors, are then believed to be required to progress the cells around the cycle. PDGF addition to cells also elicits a myriad of responses, although it is still not clear if all of these responses are required to elicit the mitogenic response. Structurally, PDGF consists of two non-identical subunits, designated the A and B chains, which are linked by disulfide bonds. Its molecular weight is between about 28-35,000 Daltons, depending on the degree of glycosylation of the sample. Separation of the subunits is believed to result in total loss of biological activity. Recently, it has been suggested that the B chain of PDGF is highly homologous to the predicted protein sequence of the oncogene (v-sis) of simian sarcoma virus (SSV). Indeed, SSV-infected cells either store or secrete a growth factor which is immunologically similar to PDGF. The biosynthesis of this protein has been studied in SSV transformed cells and has been shown to undergo extensive processing, although the major form appears to be a protein of 28,000 Daltons. Two distinct cell surface receptors for PDGF have been identified and are present on smooth muscle cells, fibroblasts, and glial cells. Both PDGF receptors contain tyrosine kinase activity, as has been shown for both the EGF and insulin receptors. It has recently been demonstrated that either the A or the B chain of PDGF is sufficient for mitogenesis. Interestingly, both normal cells and transformed cells have been shown to secrete PDGF-like mitogens into the culture media. It seems likely that growth factors, including PDGF, have some role in normal cellular development, differentiation and tissue repair. The autonomy of transformed cells may be related to endogenous production of growth factors, including PDGF, which may lead to autocrine stimulation and constant stimulation of cell growth.

Fibroblast growth factor (FGF) was initially identified in 1975, Gospodarowicz, D.: *J. Biol. Chem.*, 250:2515-2520 (1975). However, its exact chemical nature has remained obscure until only recently. At least seven (7) forms of FGF have now been identified wherein aFGF and bFGF represent the major forms. One major form is of an acidic nature, i.e., aFGF (pI=5.8), the other major form is basic, i.e., bFGF (pI=9.6). Both forms are present in bovine brain, and the basic form has also been found in bovine pituitary. It is also possible that bFGF may be present in platelets as well. Both species of FGF will stimulate the growth of cells of mesodermal origin, although their potencies are different. The biological effects of FGF reported in the past are now being re-examined, as preparations used in the past were not pure. What is certain, however, is that FGF will stimulate both fibroblast and endothelial growth, as well as repress cell differentiation in cultured muscle cells. No data, however, is believed to be available concerning the biosynthesis of FGF.

The transforming growth factors (both alpha and beta) have very interesting properties. TGF-alpha was first found to be secreted by various transformed cells, and has since been shown to interact with epidermal growth factor (EGF) receptors, and to be structurally (although not antigenically) similar to EGF. TGF-alpha will elicit the same intracellular events as EGF, including cellular proliferation via binding to the EGF receptor. The molecular weights of various species of TFG-alpha vary from about 6,000 to about 11,000 Daltons, and all consist of single polypeptide chains. Recently, a higher molecular weight form (about 25,000 Daltons) of TGF-alpha has been identified in platelets. This may represent a precursor form of other TGF-alphas, although this has not yet been conclusively demonstrated. TGF-alpha, in conjunction with TGF-beta, will allow fibroblasts to grow in soft agar, which is a typical property of transformed cells. Neither TGF-alpha nor TGF-beta individually can do this. TGF-beta has a molecular weight of 25,000 Daltons and consists of a homodimer. The subunits are held together by many disulfide linkages, and destruction of the linkages leads to a loss of biological activity. TGF-beta is also found to be secreted by transformed tissues. Platelets are a major storage site for TGF-beta. Three distinct cell surface receptors for TGF-beta have now been identified by cross-linking studies. The biological effects of TGF-beta are quite complex. The first biological effect noted was the ability of TGF-beta in conjunction with either EGF or TGF-alpha, to stimulate fibroblast growth in soft agar, which is a phenotypic trait of transformed cells. Since then TGF-beta has been shown to also inhibit both normal and transformed cell growth, possibly by lengthening the $G_1$ phase of the cell cycle, although the target cell density also appears to play an important role in the effect of TGF-beta activity on the cell. TGF-beta will, by itself, stimulate DNA synthesis in serum-deprived, sparse fibroblast cultures. However, TGF-beta will not stimulate DNA synthesis in confluent, density arrested fibroblast cultures. The reason for the distinction has not yet been established. TGF-beta will also affect EGF receptor metabolism. Short-term treatment, i.e., about 1-4 hours, of rat fibroblasts with TGF-beta can decrease the number of high-affinity sites for EGF. Further treatment with TGF-beta results in an overall increase in EGF receptor number for both the low and high-affinity sites. The increase in EGF receptor number by TGF-beta appears to account for a synergistic response to the combination of TGF-beta and EGF, as measured by DNA synthesis in the recipient cells. How these alterations in EGF receptor number are brought about, or the mechanism of synergy between TGF-beta and EGF, are at present unknown.

One problem in studying the effects of PDGF, TGF-alpha and TGF-beta on cells in culture is the difficulty in obtaining large quantities of each factor which is a typical problem associated with proteins generated by cells as indicated above. The major storage site, in normal tissue, for these factors is the platelet. It is not only difficult to obtain large quantities of platelets for large-scale purification, but even if such quantities of platelets could be obtained, platelets presently cannot be used as a practical matter to study the biosynthesis, storage and/or release of these factors. With respect to natural TGF-beta, it can be obtained from bovine kidney (1 kg of kidney will generally yield 3-4 micrograms of TGF-beta) and FGF can be isolated in microgram levels from bovine brain or pituitary. Unfortunately, it is difficult to do biosynthetic studies in these tissues as well. Thus, the establishment of a cell line which can synthesize these factors in generous quantities as well as provide an ample source for the genes and messenger RNAs would be very advantageous for their production and biosynthetic and physiological studies. Certain cell lines (primarily osteosarcomas) have been identified hitherto which are believed to secrete a PDGF-like molecule, Seifert, R. et al: *Nature*, 311:669-781 (1984); Di Corleto, P. E. et al: *Proc. Natl. Acad. Sci. USA*, 80:1919-1923, 1983; and Bowen-Pope, D. F. et al: *Proc. Natl. Acad. Sci. USA*. 81:2396-2400 (1984). However, it is presently believed that to date no cell lines comprised of monophenotypic cloned cells of megakaryocytic lineage and origin, which are believed to be platelet precursors, have been well characterized or established.

The development of an in vitro cell line of megakaryocytic lineage unfortunately has proven to be very difficult. Normal human megakaryocytes can be isolated and grown in tissue culture, Duperray, A. et al: *J. Cell Biol.*, 104:1665 (1987); Mazur, e. et al: *Exp. Hematol.*, 15:340 (1987); Berkow, R. L. et al: *J. Lab. Clin. Med.*, 103:811 (1984); Kimure, H. et al: *J. Cell Phys.*, 118:87-96, 1984; and Tabilo, A. et al: *EMBO J.*, 3:453-459 (1984). But generally, these cultures can only be maintained for short periods of time, and it is difficult to produce large quantities of cells. Some permanent cell lines with megakaryocytic-like features have been suggested, Tabilo, A. et al: *EMBO J.*, 3:453-459 (1984), and Gerwirtz, A. et al: *Blood*, 60:785-789; however, these cell lines have been derived from patients with nonmegakaryocytic leukemias and show only limited megakaryocytic differentiation. In a recent report by Morgan D. A. et al: *J. Cell. Biol.*, 100:565-573, (1985), they have suggested therein that human cell lines have been developed with properties similar to megakaryocytes. These cell lines, however, are believed to be derived from patien's with either various hematologic disorders or normal peripheral blood. They do not show the morphologic features of mature megakaryocytes, though the initial unconfirmed immunohistochemical studies possibly show a population of cells with megakaryoblastic features. These cell lines have been analyzed for cross-reacting material to an antibody directed against PDGF, Pantazis, P. et al: In *Cancer Cells*, Vol. 3, J. Feramiso, B. Ozanne, and C. Stiles, eds., Cold Spring Harbor laboratory, pp. 153-157, 1985. Intracellular proteins in the range of 12,000-48,000 Daltons were detected, although the mitogenic capability of these proteins has not yet been reported, nor was it reported if this cell line expresses large quantities of these growth factors.

There have also been other recent reports drawn to cell lines alleged to have megakaryocyticlike features. For example, a cell line originating from bone marrow and designated as EST-IU is disclosed in Sledge, G. et al: *Cancer Res.*, 46:2155 (1986); and Roth, B. J. et al: *Blood*, 72:202 (1988). This EST-IU cell line, however, is not cloned, it is not immortal, i.e., it dies upon continuous culturing, and it has a karyotype of 84. Another cell line designated as DAMI is disclosed in Greenberg, S. M. et al: *Blood*, 72:1968 (1988). It is reported that the DAMI cell line is originated from circulating blood, it is not a cloned cell line, it expresses the erythroid marker glycophorin, and it has a variable karyotype of 54-64 chromosomes. The cell line designated as CMK has been disclosed in Komatsu, N. et al: *Blood*, 74:42 (1989). Komatsu, N. et al reports that the CMK is originated from circulating blood, it expresses the monocyte marker OKM5, PMA induces it to express the erythroid marker glycophorin A, and only about 20% of its cells are positive for the gpIIbIIIa protein complex. The literature has also reported the cell line designated as MEG-01 in Ogura, M. et al: *Blood*, 66:1384 (1985). The MEG-01 cell line is originated from bone marrow, it is not cloned, it expresses the monocyte marker BA-1, and the chromosome number of its cells vary between 56–58. In addition, the MEG-01 cell line has been subsequently cloned into a cell line designated as MEG-01s. However, only about 25% of the cells of the MEG-01s cell line express the gpIIbIIIa protein complex. In addition, the other characteristics of the MEG-01 recited above are featured by the cloned cells of the MEG-01s cloned cell line. A cell line designated as T-33 has also been recently reported by Tange, T. et al: *Cancer Res.*, 48:6137 (1988). The T-33 cell line, however, is originated from blood, it is not cloned, only about 13% of the cells thereof express platelet peroxidase, and it has a karyotype of 51.

Consequently, it would be very desirable to establish xenografts and in vitro cell lines which are monophenotypic for megakaryocytic lineage for providing ample quantities of growth factors, genes and messenger RNAs as well as to assist in the study of megakaryocytes, megakaryocyte associated functions, megakaryopoiesis and megakaryocytic properties expressed by megakaryocytes.

SUMMARY OF THE INVENTION

In brief, the present invention alleviates certain of the above mentioned problems and shortcomings of the present state of the art through the discovery of a novel continuous monophenotypic human xenograft and novel continuous monophenotypic human in vitro cell lines that are of megakaryocytic lineage and origin, and which are capable of producing a variety of proteins, including certain growth factors.

The established human xenograft of the present invention, designated as CHRF-288, was initially obtained from soft or extramedullary orbital metastasis tissue biopsied from a human infant patient diagnosed as having acute megakaryoblastic leukemia and myelofibrosis. Histologically, the CHRF-288 xenograft comprises cells that are morphologically similar to cells of megakaryoblasts and immature megakaryocytes. More particularly, the CHRF-288 xenograft comprises pleomorphic cells with single convoluted nuclei or multilobed nuclei, prominent granular cytoplasm and an alveolar histologic pattern in some areas. Ultrastructurally the multilobed nuclei contain prominent nucleoli and the cytoplasmic granules contain the characteristics of granules found in megakaryocytes and platelets, which are known to be storage sites of platelet-derived growth factor. The cells of the CHRF-288 xenograft are believed to be homogenous, as about 98% of the cells stain with the appropriate antibodies specific for identifying platelets and other cells of the megakaryocytic series. The cells of the CHRF-288 xenograft express Factor VIII, gpIIbIIIa protein complex, platelet peroxidase, which is an enzyme unique to platelets and megakaryocytes, granular membrane protein-140, transforming growth factor-beta and basic fibroblast growth factor. On the other hand, the cells of the CHRF-288 xenograft do not express markers for other lineages, such as T-cell, B-cell, monocyte or erythroid lineages. The cells of the CHRF-288 xenograft do, however, react with the OKT9 marker which identifies the transferrin receptor. Nevertheless, the transferrin receptor, which regulates the transport of iron into cells, is common to a number of divergent cells irrespective of their phenotypic lineages. The cells of the CHRF-288 xenograft are therefore believed to be monophenotypic for megakaryocytes, i.e., they express markers for only megakaryocytic lineage. Moreover, it is believed that the CHRF-288 xenograft of the present invention is of megakaryocytic or platelet origin and has multiple marker characteristics of advanced or mature megakaryocytes. Quite amazingly, the CHRF-288 xenograft has been successfully passaged in athymic nude mice for over a four year interval and presently exists as a stable, continuous xenograft.

The continuous human in vitro cell lines of the present invention have been successfully established in tissue culture and cloned from individual cells derived from the CHRF-288 xenograft. The cloned human in vitro cell lines are designated as CHRF-288-1, CHRF-288-2, CHRF-288-3, CHRF-288-4, CHRF-288-5, CHRF-288-6, CHRF-288-7, CHRF-288-8, CHRF-288-9, CHRF-288-10, CHRF-288-11, CHRF-288-12, CHRF-288-13 and CHRF-288-14.

The cloned human in vitro cell line designated as CHRF-288-11 is comprised of homogenous, monophenotypic cells of megakaryocytic lineage that are morphologically similar to megakaryoblasts. More particularly, the cloned CHRF-288-11 cell line is comprised of cells which range in size from about 15 to about 20 microns in diameter and contain highly basophillic, slightly granular cytoplasms having prominent eosinophillic Golgi zones. The majority of the cells of the cloned CHRF-288-11 cell line have single oval or rounded nuclei with approximately one to three prominent nucleoli. Nevertheless, approximately 2–3% of the cells of the cloned CHRF-288-11 cell line are believed to have bilobed nuclei, and less than approximately 0.5% of such cells are believed to have complex multilobed nuclei. Although the majority of the cells of the cloned CHRF-288-11cell line are rounded, there are several cells thereof which exhibit cytoplasmic protrusions.

The cells of the CHRF-288-11 cell line are believed to be homogenous since they were cloned from a single cell derived from the CHRF-288 xenograft and exhibit a constant karyotype, i.e., 50XY. The cells of the CHRF-288-11 cell line are also believed to be monophenotypic for megakaryocytic lineage since they express markers specifically common to platelets and other cells of the megakaryocytic series. Exemplary of the markers expressed by certain cells of the CHRF-288-11 cell line are platelet peroxidase, gpIIbIIIa, platelet $Ca^{++}$-ATPase, Factor VIII, platelet factor IV, basic fibroblast growth factor (bFGF), transforming growth factor-beta (TGF-beta), beta-thromboglobulin and OKT9. Certain cells of the CHRF-288-11 cell line also express the granular membrane protein-140 (GMP-140) which is typically found in the alpha granules of normal platelets and endothelial cells. The cells of the CHRF-288-11 cell line do not express markers specifically common for other lineages, such as erythroid, T-cell and B-cell markers, nor do they react positive for myeoloperoxidase.

From a developmental standpoint, it is presently believed that the cells of the CHRF-288-11 cell line can be characterized as being at least as mature as megakaryoblasts and more particularly as colony forming unit megakaryoblasts (CFU-MEGs), but less mature than fully developed megakaryocytes of the megakaryocytic series, since such cells in addition to the above react positive for the MY7 (CD13), MY9 (CD34), MY10 (CD38) and HLA-Dr markers. Quite amazingly, the cloned in vitro cell lines including the cloned CHRF-288-11 cell line of the instant invention have been passaged in tissue culture for over a two year interval and presently exist as stable, continuous human in vitro cell lines.

The continuous megakaryocytic CHRF-288 xenograft in accordance with this invention is deposited under the Budapest Treaty with the American Type Culture Collection (ATCC), 12301 Parklawn Drive, Rockville, Md. 20852, under accession No. ATCC CRL 9139. Fourteen continuous in vitro cell lines cloned from the CHRF-288 xenograft in accordance with this invention have been designated as CHRF-288-1, CHRF-288-2, CHRF-288-3, CHRF-288-4, CHRF-288-5, CHRF-288-6, CHRF-288-7, CHRF-288-8, CHRF-288-9, CHRF-288-10, CHRF-288-11, CHRF-288-12 CHRF-288-13 and CHRF-288-14, as indicated above, and are stored in our laboratory at the University of Cincinnati, College of Medicine, Cincinnati, Ohio. The continuous in vitro cell line designated as CHRF-288-11 is also deposited under the Budapest Treaty with the American Type Culture Collection (ATCC), 12301 Parklawn Drive, Rockville, Md. 20852, under accession No. ATCC CRL 10107. Although this indicated public availability is the simplest method of obtaining the CHRF-288 xenograft, the CHRF-288-11 cell line or the other thirteen human in vitro cell lines in accordance with this invention, it is not altogether impossible or improbable that similar and functionally substantially identical xenografts or human in vitro cell lines might be produced continuously by other methods in view of the teachings of this invention. Such functionally substantially identical xenografts or in vitro cell lines may be considered to be biologically equivalent to the human CHRF-288 xenograft and the human in vitro cell lines designated as CHRF-288-1 to CHRF-288-14 and in particular the CHRF-288-11 cell line and therefore are within the general scope of the present invention. Also, such and substantially identical xenografts or in vitro cell lines, which can be obtained by those skilled in the art by modifying, cloning or subcloning the human CHRF-288 xenograft or human in vitro cell lines described and thereby provided by the present invention, without substantially altering the morphological and functional properties of the human xenograft or human in vitro cell lines or those cultivated therefrom, are within the scope of the present invention.

Certain cells of the CHRF-288 xenograft or CHRF-288-11 cell line constitutively synthesize proteins, including growth-like factors similar to those which are normally believed to be packaged in platelets, such as platelet peroxidase, transforming growth factor-beta (TGF-beta), gpIIbIIIa protein complex, Factor VIII, platelet factor IV and/or beta-thromboglobulin. In addition, certain cells of the CHRF-288-11 cell line also express basic fibroblast growth factor. The cells of the CHRF-288-11 cell line are also believed to produce platelet-derived growth factor (PDGF) when induced with, for example, phorbol 12-myristate 13-acetate (PMA) to further differentiate to a more mature form. It is also possible that the cells of the CHRF-288 xenograft and/or CHRF-288-11 cell line express other proteins and growth-like factors such as platelet-derived growth factor (PDGF) (without induction) and transforming growth factor-alpha (TGF-alpha).

The cells of the CHRF-288 xenograft and CHRF-288-11 cell line provide a continuous source of the above proteins which may or may not be naturally modified and which can be isolated by conventional ways. In addition, due to the constitutive synthesis of the proteins, such cells including those of the other thirteen human in vitro cell lines of the instant invention can provide, either directly or indirectly, a source of the genes for the proteins or growth-like factors of interest, which by conventional genetic engineering techniques, can be introduced into, for example, acceptable microorganisms for continuous large scale production of the proteins. The cells of the CHRF-288 xenograft or CHRF-288-11 cell line as well as the other thirteen human in vitro cell lines of the instant invention can also provide an ample source of the messenger RNAs as indicated above for the proteins or growth-like factors for the development of cDNAs.

The present invention also contemplates a novel method for establishing cell lines in suitable culture media through the use of a feeder layer. Generally speaking, adherent stromal cells developed in long term bone marrow culture are used as a feeder layer to produce hematopoietic growth factors and provide a microenviroment sufficient to support hematopoiesis for the initial adaption of cells derived from a solid tumor or cells of megakaryocytic lineage to in vitro culture conditions. Once adapted, however, the adopted cells are then weaned from the adherent stromal cells until they proliferate in the complete absence of any feeder layers. In practicing this unique method, the seed cells for the establishment of the human in vitro cell lines of the instant invention are derived from the CHRF-288 xenograft. As indicated hereinbefore, the cloned in vitro cell lines of the instant invention, which were derived from the CHRF-288 xenograft, are of megakaryocytic lineage and origin and are remarkably homogenous in both karyotype and marker expression.

The above features and advantages of the present invention will be better understood with reference to the following accompanying Figures, Detailed Description and Examples, which are illustrative of the preferred embodiments of the present invention.

DESCRIPTION OF THE FIGURES

With reference to the accompanying figures which are illustrative of the cells of the CHRF-288 xenograft and CHRF-288-11 cell line that are within the scope of the present invention.

DETAILED DESCRIPTION OF THE INVENTION

Figure 1:
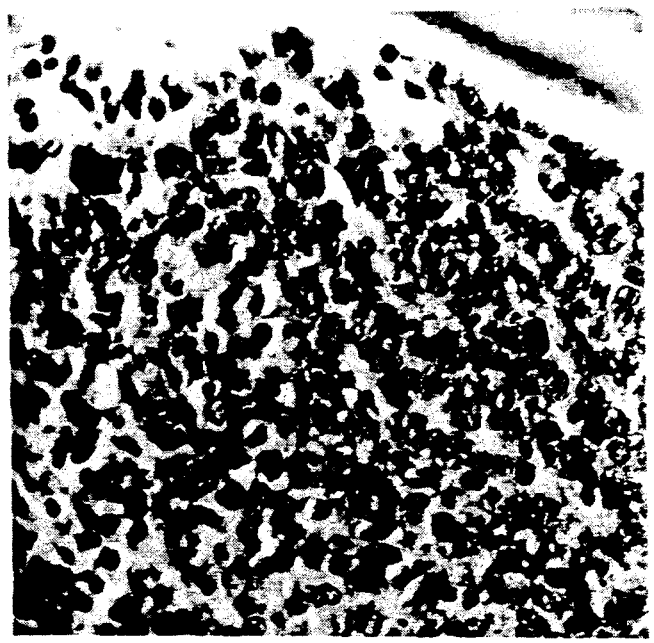
FIG. 1. Bone marrow biopsy extracted from a human infant showing replacement of the marrow by the leukemic infiltrate. The cells have pleomorphic nuclei with prominent nucleoli. Most of the nuclei are round to oval in shape though some are convoluted, and occasional multilobed nuclei are present (H&E ×485)

By way of illustrating and providing a more complete appreciation of the present invention and many of the attendant advantages thereof, the following detailed description is given concerning the novel continuous human CHRF-288 xenograft and the novel continuous human in vitro cell lines, methods of cultivating the CHRF-288 xenograft and the in vitro cell lines, and the products expressed thereby. The abbreviation "mc", which appears herein throughout, is used to reference the term "micro".

A. Human CHRF-288 Xenograft

A novel human xenograft has been restablished and designated as CHRF-288. The CHRF-288 xenograft has been established from soft tissue metastasis of megakaryocytic origin. More particularly, the CHRF-288 xenograft has been established from soft or extramedullary tissue metastasis of a human infant patient with acute megakaryoblastic leukemia and myelofibrosis. The cells of the CHRF-288 xenograft are capable of growing in athymic nude mice for indefinite periods of time while maintaining the properties of megakaryocytes. The morphological and cytochemical features of the CHRF-288 xenograft are characteristic of megakaryoblasts and less than completely mature megakaryocytes. Factor VIII antigen (vonWillebrand factor) is on the surfaces and in some cytoplasmic granules of certain cells of the CHRF-288 xenograft. Also, certain cells of the CHRF-288 xenograft express platelet peroxidase and demonstrate binding reactivity with antibodies directed against components of the glycoprotein gpIIbIIIa protein complex (such glycoproteins are presently believed to be limited to the membranes of platelets and other cells of the megakaryocytic series). Certain cells of the CHRF-288 xenograft are also believed to express transforming gorwth factor-beta, basic FGF and granular membrane protein-140 (GMP-140). Ultrastructively, the CHRF-288 xenograft comprises a population of monophenotypic cells for megakaryocytes of variable differentiation but with constant megakaryocytic features. Numerous granules with a "bull's eye" appearance, characteristic of megakaryocytic alpha-granules, are present in many of the more differentiated cells of the CHRF-288 xenograft. Immunoelectronmicroscopy of the CHRF-288 xenograft demonstrates binding of the anti-factor VIII related antibody to the large, alpha-granules, which are believed to be responsible for the storage of PDGF-like protein and Factor VIII related antigen. No evidence of alveolar-soft past sarcoma or rhabdomyosarcoma was observed to support a finding that the cells of the CHRF-288 xenograft of this invention were derived from those two abnormalities.

The CHRF-288 xenograft is conveniently passaged in athymic nude mice derived from NIH stock of Swiss background which are maintained in filter topped cages. With respect to the initial transplantation, a single athymic mouse, under sterile conditions in a laminar flow hood, was first anesthetized with methoxyfluorane, and delicately minced cells obtained from the soft orbital tissue mass of the human infant were transplanted subcutaneously into the mouse. The cells of the CHRF-288 xenograft grew as a solid nodule in the subcutaneous tissue, measuring approximately 3.0 cm in greatest dimension. The cells of the CHRF-288 xenograft were subsequently successfully passaged, at four week intervals, by delicately mincing portions extracted from the mice and reimplanting them into subcutaneous tissue of other athymic nude mice.

B. Human In vitro Cell Lines

Novel human in vitro cell lines have been established and are designated as CHRF-288-1, CHRF-288-2, CHRF-288-3, CHRF-288-4, CHRF-288-5, CHRF-288-6, CHRF-288-7, CHRF-288-8, CHRF-288-9, CHRF-288-10, CHRF-288-11, CHRF-288-12, CHRF-288-13 and CHRF-288-14. The human in vitro cell lines have been cloned from individual cells derived from the CHRF-288 xenograft. The cells of the human in vitro cell lines are remarkably homogenous and monophenotypic for megakaryocytes of variable differentiation but with constant megakaryocytic features, and are capable of growing in tissue culture for extended periods of time while maintaining the properties of megakaryocytes.

Generally speaking, the establishment of the human in vitro cell lines involves the use of feeder layers comprising adherent stromal cells developed in long term human bone marrow (LTBM) cultures. The seed cells for the establishment of the human in vitro cell lines are derived from the CHRF-288 xenograft. The LTBM cultures are used for the initial adaption of the cells of the CHRF-288 xenograft to culture conditions. Once adapted, however, the cells are weaned from the stromal layers until they proliferate in the complete absence of any feeder layers.

Figure 13A:
FIG. 13. In vitro establishment of the CHRF-288-11 cell line. A) Control LTBM-culture prior to the addition of CHRF-288 cells. An adherent layer of stromal cells is evident without significant hematopoietic cell development. B) Isolated group of adherent stromal cells in a LTBM-culture three hours after the addition of CHRF-288 cells (the round, refractile cells). CHRF-288 cells attached to the adherent stromal cells in a pattern which coincides with the cytoplasmic processes of the adherent stromal cells (arrows). Several non-adherent CHRF-288 cells are present in the upper area of this field. C) LTBM-culture three days after the addition of CHRF-288 cells. Numerous, viable CHRF-288 cells are present and attached to the adherent stromal cells. D) LTBM culture 12 days after the third transfer of CHRF-288 cells into new LTBM-cultures. This is approximately 4 months after the initial establishment of CHRF-288 cells in culture. All photographs were taken using Hoffman modulation optics (Mag: ×245)

The adherent bone marrow stromal cells in LTBM cultures, which are used as the feeder layers, are developed from human bone marrow mononuclear cells (BMMCs). The BMMCs are established as discussed in detail in Example II hereinafter. Generally speaking, the LTBM cultures are established by plating BMMCs in tissue culture flasks containing LTBM media, which comprises Fischer's complete media for leukemic cells, 25% horse serum and 1% penicillin/streptomycin, and 1 micromolar hydrocortisone until adherent stromal layers develop from these cultures. During the development of the LTBM cultures, the non-adherent cells are being constantly removed to select against long-term development of hematopoietic cells. In addition, the cultures are fed weekly by removal of all media and replacement with fresh LTBM media. The hydrocortisone is removed from the culture media after about four weeks of culture, and always prior to the use of a culture as a feeder layer. The adherent stromal layers that develop from these cultures comprise fibroblasts, adipocytes and macrophages, as illustrated in FIG. 13A. The establishment of the LTBM cultures is also discussed in greater detail in Example II hereinafter.

Figure 13B:
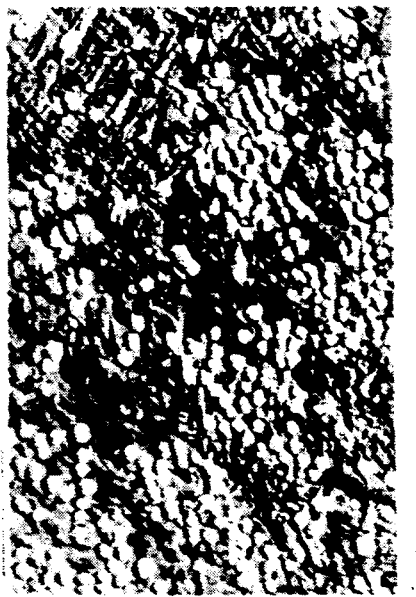
Figure 13C:
Figure 13D:

To adapt the cells of the CHRF-288 xenograft to in vitro growth, the LTBM cultures are inoculated with cell suspensions derived from the CHRF-288 xenograft. The cells from the CHRF-288 xenograft rapidly attach to the LTBM feeder layers and proliferate, forming large colonies of cells attached to the adherent stromal cells, as depicted in FIGS. 13B, 13C and 13D. Cell growth is vigorous and nearly confluent monolayers of cells develop over the stromal layers. Cultures are fed weekly by complete replacement of LTBM media with fresh media. Once confluent, the cells are shed into the medium, and are replated onto new LTBM cultures without any cessation of cell proliferation. The initial seeding densities of the cell suspensions should be high, approximately $10^5$ cells/flasks, since it is believed that cell proliferation will not occur at low densities.

The cells of the CHRF-288 xenograft, which form the confluent monolayers, are weaned from the adherent stromal cells over a period of for example four months. This is accomplished by collecting and plating cells which are spontaneously released from the adherent stromal cells onto new culture dishes in the absence of stromal cells. Notwithstanding, some stromal cells are carried over by this limiting dilution procedure and attach to the flask and proliferate. Many of the CHRF-288 cells, however, remain unattached to the carried-over stromal cells, and this process of replating is repeated until no further stromal cells are being carried over, and the cells of the CHRF-288 xenograft develop the capacity to grow in the absence of such cells. Since the cells of the human in vitro cell lines have been weaned from adherent stromal cells in LTBM cultures, it is presently believed that the importance of stromal cell derived growth factors in the proliferation of the cells of the human in vitro cell lines diminishes with continuous culturing, and that the cells of the human in vitro cell lines themselves are producing autocrine growth factors.

The cells of the established CHRF-288-11 in vitro cell line are monophenotypic for megakaryocytic lineage as determined by a wide variety of criteria, and as indicated in FIGS. 15-19 and Table 9. The karyotype of the cloned CHRF-288-11 cells is 50, XY, +6q−, +8, +17, +21, 21p+, −10, +19p+, −15, 1p+, 6p−. The karyotype of the cloned CHRF-288-11 cells demonstrate trisomy for chromosomes 6, 8, 17, 19 and 21. The extra chromosome 6 of the cells of the CHRF-288-11 cell line has a large deletion, and trisomy for chromosome 19 is variable. The only differences in chromosomes between the cloned CHRF-288-11 cells and the original CHRF-288 xenograft cells are believed to be a small 6p deletion (p23) and the loss of one chromosome 10 in the CHRF-288-11 cells.

Figure 15A:
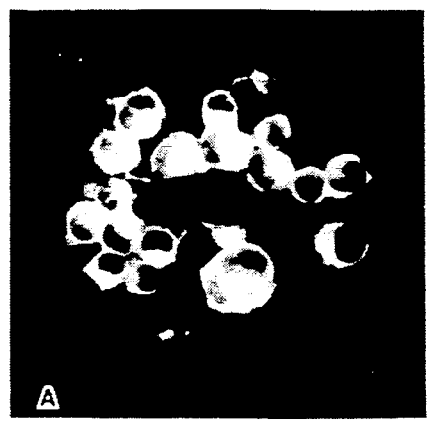
FIG. 15. Immunohistochemistry of cultured CHRF-288-11 cells. Panel A shows positive fluorescence of a group of cultured CHRF-288-11 cells after incubating cells with monoclonal antibody T-10 which identifies platelet gpIIbIIIa protein complex. Panel B is a photomicrograph showing immunofluorescence of a group of CHRF-288-11 cells following incubation with anti-Factor VIII related antigen primary antibody. The positive reaction is primarily cytoplasmic in distribution. Panel C demonstrates platelet factor IV (PF4) immunoreactivity, and panel D demonstrates the platelet-specific $Ca^{++}$-APase or PF4. The CHRF-288-11 cells were briefly permeabilized in acetone. Controls using non-specific antibodies as the primary label were negative for fluorescence (not shown) (Magnification: all panels at ×300)
Figure 15B:
Figure 15C:
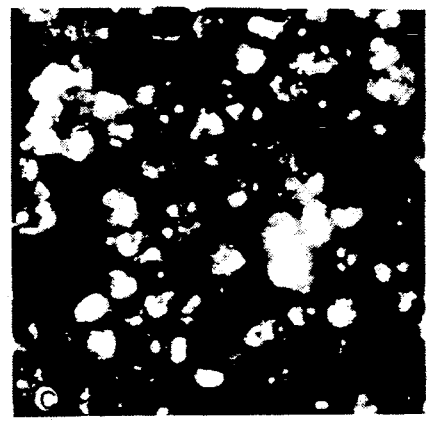
Figure 15D:
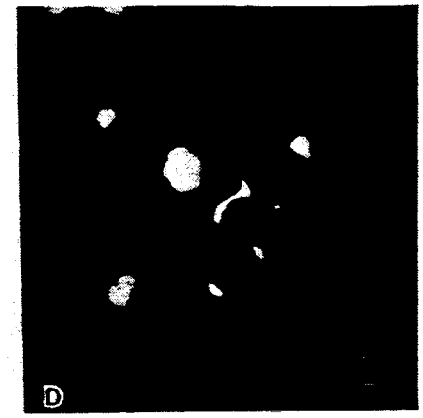

The morphological and cytochemical features of the CHRF-288-11 cell line are characteristic of megakaryoblasts and more particularly colony forming unit megakaryoblasts (CFU Megs) and less than completely mature megakaryocytes. The cells of the CHRF-288-11 cell line range in size from about 15-20 microns in diameter, contain highly basophilic, slightly granular cytoplasms with prominent eosinophilic perinuclear Golgi zones. Most of the cloned CHRF-288-11 cells have single oval or rounded nucleus with one to three prominent nuclei. Some cells of the CHRF-288-11 cell line have bilobed nuclei (approximately 2-3% of the total number of cells), and a few CHRF-288-11 cells have complex multilobed nuclei (less than about 0.5% of the population). Several CHRF-288-11 cells have cytoplasmic protrusions, although the majority of such cells are rounded. It is presently believed that greater than about 95% of the cells of the CHRF-288-11 cell line express platelet gpIIbIIIa protein complex, and approximately 30-40% of the population expresses Factor VIII, which are characteristic of both platelets and megakaryocytes (see FIGS. 15A and 15B). Those CHRF-288-11 cells which express Factor VIII are thought to be the generally larger, more mature cells. Nonetheless, many immature CHRF-288-11 cells which show little cytologic evidence of maturation also express Factor VIII. The cloned CHRF-288-11 cells also express platelet factor IV (PF4) (FIG. 15C), as well as platelet Ca++-ATPase (FIG. 15D). In contrast to Factor VIII, PF4 is generally expressed in most CHRF-288-11 cells, although there is more cell to cell variability. It is also believed that greater than approximately 80% of the cloned CHRF-288-11 cells express platelet peroxidase. The cells of the CHRF-288-11 cell line do not produce myeloperoxidase.

Electron microscopy reveals that most of the cloned CHRF-288-11 cells have a single nucleus with a single prominent nucleolus and the chromatin is moderately condensed (see FIGS. 16A, 16B, 16C and 16D). Most CHRF-288-11 cells contain few cytoplasmic organelles other than large numbers of polyribosomes. The more mature CHRF-288-11 cells (see FIG. 16A) generally have extensive rough endoplasmic reticulum, frequent mitochondria, and well developed Golgi complex associated with numerous small vessicles, some of which are coated. There are also numerous granules that vary in size and electron density. Small, round granules (about 100-300 nm) are evident, and contain an electron dense matrix that either completely fills the granules or is surrounded by clear halos in the more differentiated cells of the CHRF-288-11 cell line. These granules are typically budding near the Golgi complex, but occasionally arise from areas of the endoplasmic reticulum in the periphery of the CHRF-288-II cells (see FIG. 16C). Ultrastructural features of the small dense granules resemble the various stages of platelet dense granule formation. Larger granules (about 300-600 nm), resembling alpha-granules, have a diffuse finely granular matrix and occasionally a moderately dense nucleoid (see FIG. 16B). Platelet peroxidase expression is believed to be localized to the perinuclear zone and in the endoplasmic reticulum.

The cloned CHRF-288-11 cells have also been examined for expression of cell surface markers characteristic of T-cells, B-cells, natural killer cells, lymphoblastic leukemia, monocytes, and megakaryocytes. The CHRF-288-11 cells express HLA-Dr backbone antigen, and have epitopes which are recognized by MY7 (CD-13) and MY9 (CD-33) monoclonal antibodies. No T- or B-cell markers are evident on the cloned CHRF-288-11 cells, nor is there evidence for expression of glycophorin A by Western Blot analysis (see FIG. 17) and immunocytochemistry (data not shown), or hemoglobin as determined by immunocytochemistry (not shown). Benzidine staining fails to reveal the presence of heme (data not shown). These data indicate that the cloned CHRF-288-11 cells are expressing megakaryocytic markers, and that they are not biphenotypic for the erythroid lineage.

The only markers expressed by the CHRF-288-11 cell line that one might not expect to find on megakaryocytes are the HLA-Dr antigen, and the MY7 (CD-13) and MY9 (CD-33) markers. However, HLA-Dr antigens are believed to be found on a variety of other cell types, such as B-cells and early stage megakaryoblasts, as reported by Mazur, E. et al: *Exp. Hemotol.*, 15:340 (1987); and Breton-Goruis, J. et al: *Blood*, 51:45 (1978). While the MY7 marker (CD-13) is believed to be primarily expressed on peripheral blood monocytes, granulocytes, 5-40% of normal bone marrow mononuclear cells, and in 80% of acute myeloid leukemia cases, the presence of MY7 (CD-13) on the CHRF-288-11 cells is not necessarily contradictory It has been recently reported that 5-10% of megakaryoblastic leukemia cases which are positive for gpIIbIIIa protein complex are also positive for MY7 (CD-13). See San Miguel, J. F. et al: *Blood*, 72:402 (1988). This suggests that early cells of megakaryocytic origin often express both markers. Thus, the presence of the MY7 (CD-13) marker is believed to indicate the immature aspect of the CHRF-288-11 cell line, and it is further believed that if the cloned CHRF-288-11 cells are induced to differentiate to a more mature form, the expression of this marker will decease. Since the presence of the MY9 (CD-38) marker is similar in cell expression to the MY7 (CD-13) marker, it is believed that the MY9 (CD-13) marker also indicates the immature aspect of the CHRF-288-11 cell line.

The CHRF-288-11 cell line also demonstrates a potential for hyperploidy in response to phorbol esters, such as phorbol 12-myristate 13-acetate (PMA) (see FIG. 19). In a normal cell cycle pattern the S phase and 4N cells are expected to decrease as the rate of proliferation also decreases. However, under conditions of PMA treatment of the CHRF-288-11 cells, in which the proliferation rate decreases by 60%, the number of cells in the S and 4N phases actually increase, and many cells exhibit ploidy values of greater than 4N. These data indicate that there is a transgression from the cell cycle pattern, and that many of the cells fall into a pattern of nuclear replication without cytoplasmic division, which is consistent with megakaryocytic development. In view of this response, it is presently believed that the cells of the CHRF-288-11 cell line undergo further differentiation to a more mature form when exposed to the phorbol esters. In addition, the CHRF-288-11 cell line expresses a factor similar to platelet derived growth factor (PDGF) when induced by PMA.

C. Products of the Human CHRF-288 Xenograft and The Human In Vitro Cell Lines The CHRF-288 xenograft and CHRF-288-11 are unique in generating products known to be elaborated by platelets. Certain cells of the CHRF-288 xenograft and CHRF-288-11 cell line constitutively produce proteins having different physiological activities in isolatable amounts. For example, certain cells of the CHRF-288 xenograft are believed to express products similar to bFGF, TGF-beta, Factor VIII, GMP-140, gpIIbIIIa protein complex and platelet peroxidase. Certain cells of the CHRF-288-11 cell line are believed to express products similar to bFGF, TGF-beta, Factor VIII, platelet factor IV, platelet peroxidase, beta-thromboglobulin, gpIIbIIIa protein complex, platelet CA++-ATPase, GMP-140, MY7, MY9, MY10, OKT9, and HLA-Dr antigens. Certain cells of the other thirteen human in vitro cell lines of the present invention are believed to express products similar to gpIIbIIIa protein complex and Factor VIII. Thus, the CHRF-288 xenograft and CHRF-288-11 cell line provide sources for the production of polypeptides of physiologic interest. In addition, because of the constitutive production of these polypeptides by the CHRF-288 xenograft, the CHRF-288-11 cell line and possibly the other cloned in vitro cell lines of the instant invention, it is believed that they make available the genes and the messenger RNAs for these or other polypeptides in relatively large amounts. For example, certain cells of the CHRF-288-11 cell line have been determined to express mRNAs encoding proteins similar to PDGF-A chain, basic fibroblast growth factor, transforming growth factor-beta and transforming growth factor-alpha. By employing conventional techniques, the genes and messenger RNAs for selected polypeptides may be separated from the mass of genes and messenger RNAs present. Once isolated, the selected genes can be used to transform microorganisms for production of such polypeptides, and the selected messenger RNAs can be used for production of cDNAs in accordance with techniques available in the art.

In describing the various products produced by the CHRF-288 xenograft and CHRF-288-11 cell line, the case history and cell tissue evaluation relative to the CHRF-xenograft will be first discussed. The direct production of the polypeptides by the CHRF-288 xenograft will then be discussed. This will then be followed by two examples. Example I concerns a description of the extraction of the initial cells from the orbital tissue of the human infant patient and the continuous cultivation of those cells in athymic nude mice to generate the stable continuous CHRF-288 xenograft. The second Example II concerns the propagation of the CHRF-288-11 cell from the human CHRF-288 xenograft, examination and characterization of the cells of the CHRF-288-11 cell line, and the products expressed by the CHRF-288-11 cell line.

D. Case History

A white human male infant was well until the age of 17 months when he developed generalized irritability and fever. He was first evaluated at the University of Kentucky Medical Center and had a WBC of 12,700/mm$^3$ with a normal differential, Hgb of 9.1 gm/dl, and platelet count of 22,000/mm$^3$. The direct and indirect Coombs were negative and titers to CMV and EBV were nondetectable. A bone marrow aspirate was hypocellular, with a few atypical cells. Repeat bone marrow studies including biopsy revealed myelofibrosis with scattered areas of normal hematopoiesis; a few areas of undifferentiated atypical cells were noted. Chromosome analysis of the heterogenous bone marrow population revealed hyperdiploidy; consistent duplication of chromosomes 2, 6, 7, 8 and 21 as well as a reciprocal 12 p:15q translocation. The Hgb F was 0.9%, LDH 786 IU, B$_{12}$ 532 ng, and serum neuraminadase 7 mg/ml. Additional studies included normal chest x-ray, normal abdominal ultrasound, negative skeletal survey and negative bone scan. A 24 hour urine collection for catecholamine metabolites was normal.

He was referred to Children's Hospital Medical Center in Cincinnati, Ohio at 18 months of age for further evaluation and consideration for bone marrow transplantation. A repeat blood count revealed a WBC of 21,800/mm$^3$ with 38% undifferentiated cells. The Hgb was 9.4 gm/dl and the platelet count 15,000/mm$^3$. A bone marrow aspirate showed 26% leukemic blast cells. Special stains showed blast forms to be weakly PAS positive, alpha-napthol esterase positive, peroxidase negative and chloracetate esterase negative. Bone marrow biopsy was 90% replaced with abnormal blast cells; no increase in reticulin fibers was noted. Radiographs demonstrated lytic lesions of the proximal humeri, as well as leukemic lines with areas of periosteal elevation. A tentative diagnosis of acute monoblastic leukemia was made.

The patient was placed on Children's Cancer Study Group protocol 213P, he was randomized to the "Denver" arm (Daunomycin 0.67 mg/kg×3 days, Ara-C 3.3 mg/kg×5 days; 6-thioguanine 1.67 mg/kg×5 days, VP16-213 5 mg/kg×2 days and dexamethazone 0.2 mg/kg/×5 days). Bone marrow studies on day 14 revealed a hypocellular aspirate, biopsy showed a marked reduction in the number of leukemic cells and a predominance of collagen and reticulin. Twenty-eight days after beginning chemotherapy, the patient started cycle #2 of the "Denver" regimen. Repeat bone marrow studies two weeks later demonstrated decreased marrow cellularity and continued replacement with fibrious tissue.

The patient's induction course was subsequently complicated by *Streptococcus viridans* sepsis, *Pseudomonas bacteremia, Pseudomonas perirectal* abscess, and *Herpes simplex* viremia.

Despite the two cycles of chemotherapy, he developed hepatosplenomegaly, progressive bony lesions and a left proptosis. CT scan of the head 8 weeks after admission revealed the latter to result from a 3×3 cm mass that extended from the left ethmoid sinus to the inferior aspect of the left orbit with extensive erosion of the sphenoid bones. Bone marrow studies contained increased replacement by blast cells and further increase in fibrosis. Biopsy of the orbital mass demonstrated marked cytologic pleomorphism, and a nesting pattern with delicate fibrovascular septa. This pathology was suggestive of an unusual sarcoma or lymphoma. In consideration of these findings and the unsatisfactory response to prior chemotherapy, the patient was started on a chemotherapy regimen of: Vincristine 2 mg/m$^2 \times$1 day, Actinomycin-D 15 mcg/kg/d$\times$5 days, and cyclophosphamide 10 mg/kg$\times$3 days (VAC). He also received 600 rads (of a planned 3000 rads) to the left orbit. Upper airway compromise due to metastatic tissue compression of the posterior cervical trachea necessitated intubation Days 62 through 85 of the hospitalization.

The patient had an initial response with marked decrease in the size of soft tissue masses and complete disappearance of airway compression by twenty-six days after VAC was started.

Repeat head CT scan thirty-three days after initiation of VAC therapy showed persistence of the left orbital tumor. Skeletal survey at this time demonstrated progressive bony disease. With consent of the parents, no further therapy was administered and the patient expired 3 months after admission. A postmortem examination was not obtained.

1. Cell Tissue Evaluation

With respect to an evaluation of the morphology of the cells, bone marrow aspirate smears using conventional techniques were stained with Wright stain, Sudan Black, nonspecific esterase, acid phosphatase and peroxidase. Bone marrow biopsies, i.e., bone marrow cores, were fixed briefly in B-5 fixative and decalcified in buffered formalin with Ca-EDTA prior to paraffin embedding and sectioning. The sections were stained with H&E, PAS, reticulin and Masson trichrome stains using conventional techniques.

The initial bone marrow aspirates contained approximately 25% undifferentiated cells characterized by about 10 to about 30 mm diameter, round to slightly lobulated nuclei with about one to about two nucleoli, basophilic cytoplasm, azurophilic granules which were PAS positive and diastase resistant and prominent perinuclear Golgi zones. There was no reactivity with the chloracetate esterase and peroxidase stains, but there was weak activity of the alpha-napthol esterase stain and strong activity of the acid phosphatase stain.

The initial bone marrow biopsy showed replacement of the normal marrow by tumor cells as illustrated in FIG. 1 with oval to irregularly shaped nuclei that were variable in size and surrounded by a small to moderate amount of eosinophilic cytoplasm. Admixed with these were numerous cells with large pleomorphic, multilobulated nuclei and prominent eosinophilic, granular cytoplasm, resembling small atypical megakaryocytes. The reticulin stain showed a diffuse marked reticulin fibrosis. Initially, following the institution of chemotherapy there was a dramatic decrease in the number of leukemic cells but numerous atypical megakaryocytes persisted. Three months after beginning chemotherapy, the marrow became infiltrated by malignant cells, including cells with multilobed nuclei and prominent granular cytoplasm typical of dysplastic megakaryocytes. Many of the poorly differentiated cells and most of the well differentiated tumor cells showed strong reactivity with the PAP stain for factor VIII antigen. A postmortem bone marrow biopsy showed persistence of the leukemic infiltrate although the cellularity was markedly decreased.

Examination of the orbital tissue, initially obtained from the human infant, was conducted with light microscopy. Fresh tissue samples obtained from the orbital mass were fixed in buffered formalin, B-5 fixative or snap frozen in liquid nitrogen using conventional techniques. Paraffin embedded tissue was sectioned at a thickness of about 4 microns. Frozen tissue was sectioned in a cryostat at about 4 to about 6 microns. Paraffin sections were stained with hematoxylin and eosin (H&E), Periodate acid-Schiff (PAS), Jones modified Methenamine silver, Grimelius, and Wilder's reticulin method also using conventional techniques. Frozen section histochemistry for acid phosphatase, chloroacetate esterase (Leder) and nonspecific esterase activity (alpha-napthol esterase) was performed in the standard fashion.

Figure 2:
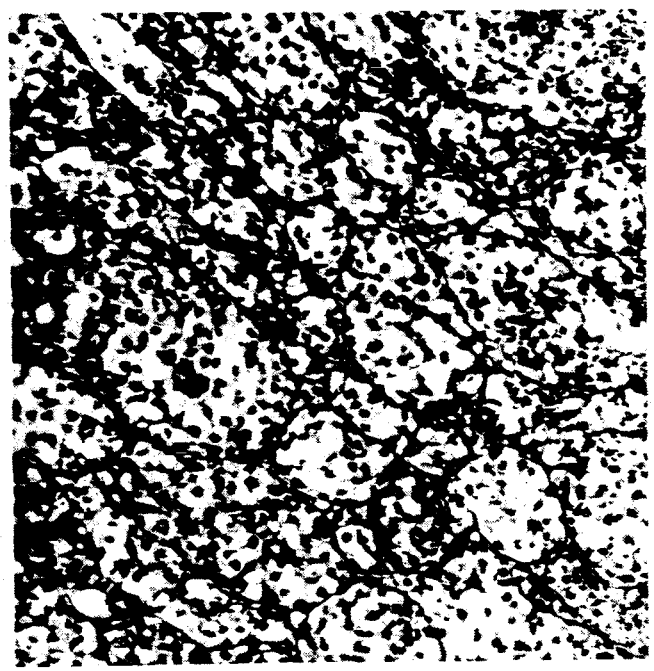
FIG. 2. Histologic appearance of orbital metastasis extracted from the infant. The tumor infiltrate has an alveolar pattern with nests of tumor cells separated by a delicate reticulin network (Reticulin ×150)

The orbital tissue contained malignant cells with highly pleomorphic nuclei, some convoluted and containing about 1 to about 3 prominent nucleoli. The infiltration varied, ranging from solid sheets of cells to areas with nests separated by a delicate fibrovascular septa; in occasional areas with loss of cell cohesion, there was an alveolar pattern, sharply defined in the reticulum stain as can be viewed in FIG. 2. The cytoplasm of the larger cells was granular in appearance with coarse granules that were diesterase resistant and PAS positive, and with fine granules that stained with the Grimelius stain. The cells showed no chloracetate esterase or alpha-napthol esterase activity although there was strong acid phosphatase activity throughout the infiltrate. Immunohistochemistry showed strong reactivity with anti-human factor VIII antigen antibody.

Figure 3:
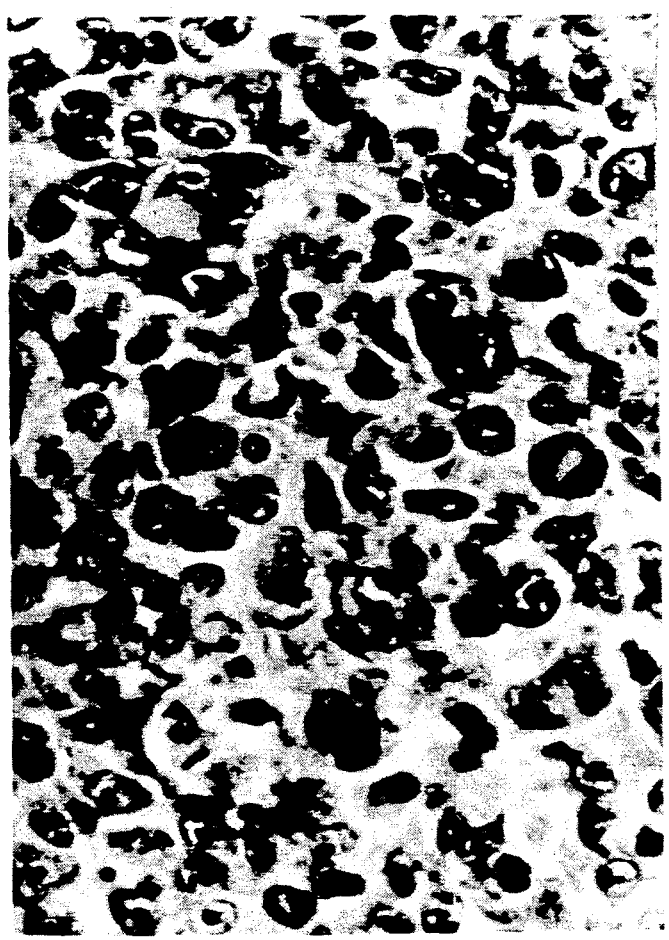
FIG. 3. Cells of this invention obtained from the nodular tissue removed from an athymic nude mouse. The tissue cells contain pleomorphic nuclei with prominent nucleoli. A granular chromatin pattern with clearing around prominent nucleoli is present in many of the cells. Convoluted nuclei as well as bilobed and multilobed nuclei are frequent. Tissue cells, characteristically have abundant granular cytoplasm with a prominent hof. (H&E ×800)

With respect to the initial orbital tissue transplanted into the single mouse, it grew as a solid nodule in the subcutaneous tissue, measuring approximately 3.0 cm in greatest dimension as indicated above. The orbital tissue was successfully passaged in other nude mice. The light microscopy of the nude mouse tissue implants was very similar to that of the orbital metastasis as shown in FIG. 3 consisting almost entirely of solid sheets of cells, only occasional small blood vessels and scant fibrous stroma. An alveolar arrangement of orbital tissue cells, however, was not a component of the nude mouse tumor implants. Poorly differentiated cells, which were most numerous, had a large single round to oval nucleus, usually one large eosinophilic nucleolus and a chromatin pattern that was finely granular with some clearing around the large nucleolus. These cells had a moderately prominent amphophilic to eosinophilic granular cytoplasm with prominent perinuclear Golgi zones. Numerous mitotic figures, some atypical, were present as were necrotic cells. The better differentiated cells contained either a single large, pleomorphic, convoluted nucleus with one to two prominent eosinophilic nucleoli or multilobed nuclei with up to eight lobes, forming a ring around an abundant granular cytoplasm, bearing a striking resemblance to mature megakaryocytes.

With respect to the immunohistochemistry of the cells, several conventional assays were conducted with conventional techniques. Rabbit anti-human factor VIII antibody, swine anti-rabbit antibody and rabbit PAP reagent were obtained from Accurate Chemical and Scientific Co. (Westburg, N.Y.). Paraffin sections from the soft tissue mass and bone marrow biopsies were incubated in the anti-human factor VIII antibody at a dilution of about 1/1200 followed by swine anti-rabbit antibody at about 1/20 and rabbit PAP reagent at about 1/20 for about 30 minutes each. Peroxidase activity was detected with 3 amino 9-ethylcarbazole (Sigma). Anti-factor VIII antibody was also detected with FITC conjugated goat anti-rabbit antibody (Cappel Laboratories) at a dilution of about 1/40. Frozen sections of unfixed tumor tissue were incubated in anti-gpIIbIIIa (T10), and anti GPIIb (Tab), monoclonal antibodies against the platelet gpIIbIIIA protein complex (obtained from the University of Texas Health Science Center at San Antonio), each at a dilution of about 1/100 for about 30 minutes. Primary antibody was detected with FITC conjugated anti-mouse antibody (Miles Lab) at a dilution of about 1/40 Negative controls for the anti-factor VIII antibody consisted of tissue sections incubated in normal rabbit serum at about 1/1200, and for the T10 and Tab monoclonal antibodies, incubation in normal mouse serum at a dilution of about 1/100. OKT3, 4, 6, 8, 9, 10 and 11 were obtained from Ortho Diagnostic Systems (Raritan, N.J.). B1, B2, and J5 (cALLa) antibodies, nonimmune mouse immunoglobulin (MsIgG), and fluorescein-labeled goat anti-mouse immunoglobulin were obtained from Coulter Immunology (Hialeah, Fla.). Anti-Leu M3 was obtained from Becton-Dickinson Monoclonal Antibody Center (Mountain View, Calif.). Six-micron frozen sections attached to gelatin-coated slides and dried at room temperature for about 10 minutes were rehydrated in phosphate buffered saline (PBS) for about 5 minutes and thereafter protected from drying. Monoclonal antibodies were diluted in PBS plus 5% fetal bovine serum at concentrations deemed optimal by previous titration, and incubated with the tissue sections in a moist chamber for about 30 minutes at room temperature. Primary antibody was detected with fluorescein-labeled goat anti-mouse immunoglobulin (diluted about 1:60 in PBS) in a moist chamber for about 30 minutes at room temperature. The tissue was viewed with the 100× oil immersion objective of a Leitz Laborlux 12 fluorescent microscope. Because the tissue composition was homogeneous, antibody reactivity was readily scored as positive or negative.

Figure 4A:
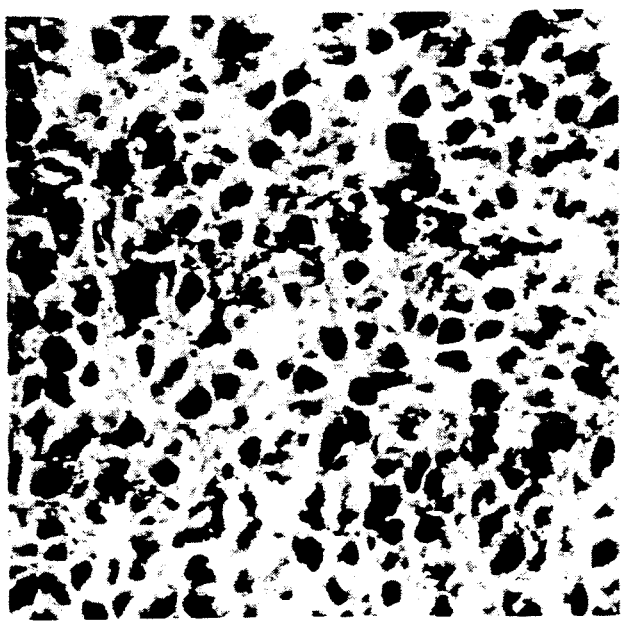
FIGS. 4a, 4b, and 4c. Immunofluorescence of the cells of this invention obtained from the nodular tissue removed from an athymic nude mouse. Monoclonal antibodies T10 (A) and Tab (B) show a uniformly distributed, finely granular label along the plasma membrane. Antiserum to Factor VIII (C) labels most cells along the plasma membrane, with intense cytoplasmic label in occasional cells (all magnifications ×600)
Figure 4B:
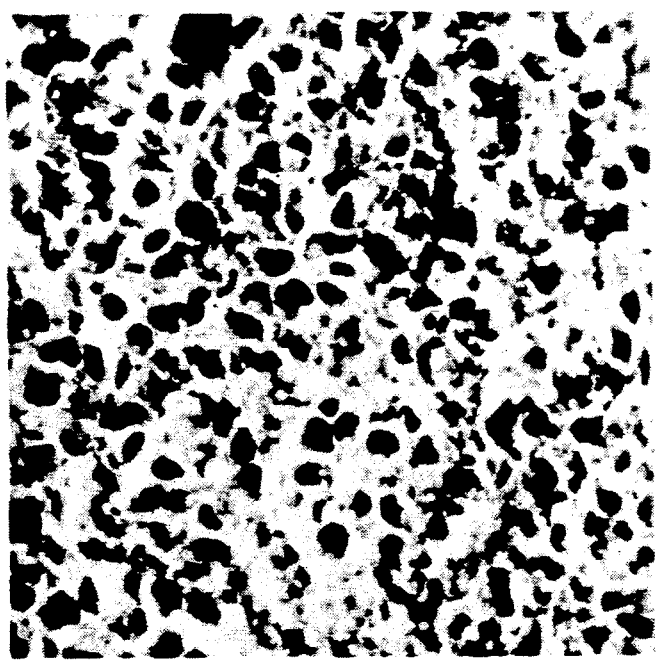
Figure 4C:

The results of histochemistry and immunohistochemistry are shown in Table I. Histochemical stains that stained the cytoplasmic granules in both the initial orbital metastasis and CHRF-288 xenograft included the PAS, Jones and Grimelius stains. Enzyme histochemistry for acid phosphatase, chloracetate esterase and alpha-napthol esterase were negative in both the original and CHRF-288 xenograft. Factor VIII related antigen was present in both the orbital tumor and the CHRF-288 xenograft and there was labeling of the cells of the CHRF-288 xenograft in the nude mouse with Tab and T10 antibodies as depicted in FIG. 4. Platelet peroxidase is also expressed by the cells of the CHRF-288 xenograft. A battery of antibodies for lymphoid and hematopoetic cell surface markers including OKT3, OKT4, OKT6, OKT8, OKT10, OKTII, B1, B2, J5 (cALLa), and Leu M3 showed no labeling of the CHRF-288 xenograft though the tumor cells of the CHRF-288 xenograft did label with antibody OKT9.

TABLE I

Histochemistry and Immunohistochemistry Results

| | Orbital Tissue | Nude Mouse Tissue (CHRF-288 Xeno-graft) |
|---|---|---|
| PAS | + | + |
| Jones | + | + |
| Grimelius | + | + |
| Acid phosphatase | + | + |
| Chloroacetate esterase | − | − |
| alpha-napthal esterase | − | − |
| anti Factor VIII related antigen | + | + |
| T10 (megakaryocytes and platelets) | ND | + |
| Tab (megakaryocytes and platelets) | ND | + |
| OKT3 (mature T-cells) | ND | − |
| OKT4 (T-cells) | ND | − |
| OKT6 (cortical thymocytes) | ND | − |
| OKT8 (T-cells) | ND | − |
| OKT9 (activated cells) | ND | + |
| OKT10 (hematopoietic stem cells) | ND | − |
| OKT11 (T-cells) | ND | − |
| B1 (B cells) | ND | − |
| B2 (intermediate B-cells) | ND | − |
| J5 (cALLa) (prepre/B-cells) | ND | − |
| Leu M3 (macrophages) | ND | − |
| MsIgG (negative control) | ND | − |
| Platelet peroxidase | ND | − |

Notations in parenthesis indicate known antigen distribution.
ND - not determined
MsIgG - Mouse serum IgG For electron microscopy evaluation, fresh tissue was obtained from the nodular tissue removed from an athymic nude mouse and was diced into about 1 mm sections and immersed in 2% gluteraldehyde in cacodylate buffer (pH of about 7.14) at about 4° C. for about two hours. The tissue was then washed in cacodylate buffer and postfixed in about 1% osmium tetroxide prior to embedding in Epon. Thin sections were stained with uranyl acetate and lead citrate and examined with a Phillips 300 electron microscope. A cell suspension for immunoelectronmicroscopy was prepared from small pieces of tumor and fixed in Periodate-lysine-paraformaldehyde (PLP) fixative. After fixation for about one hour at about 4° C., cells were washed three times in about 0.1M phosphate buffer and centrifuged in a Biofuge B microfuge (American Scientific Products) at about 2,000 rpm to form a pellet. The pellet was resuspended in peroxidase labeled rabbit anti-human factor VIII antibody diluted about 1/30 in about 0.1M phosphate buffer and incubated for about 1 hour at room temperature. Primary antibody was detected after about a 30 minute incubation period with diaminobenzidine substrate (20 mg DAB/10 ml of 0.05M tris and 0.1 and 3% $H_2O_2$) Cells were then washed in about 0.1M phosphate buffer (pH of about 7.4) and postfixed in about 1% Osmic acid in about 0.1M phosphate buffer for about 30 minutes at room temperature. The cells were then repelleted and dehydrated in alcohol and embedded in LX-112 (Ladd). Unstained sections were examined with the Phillips 300 transmission electron microscope. Control tissue was processed in an identical manner with exclusion of the primary antibody.

Figure 5:
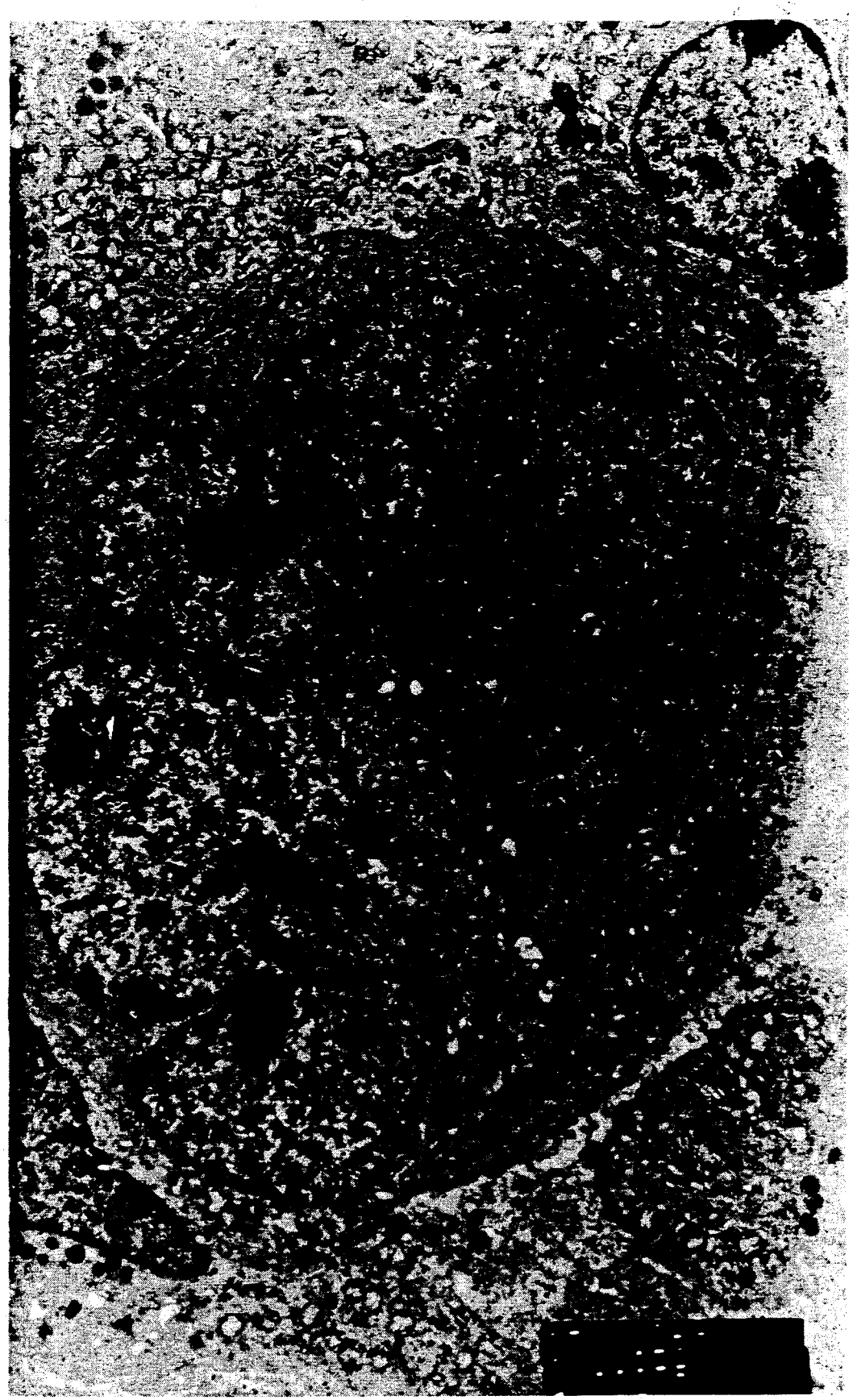
FIG. 5. Electron micrograph of cells of this invention obtained from the nodular tissue removed from an athymic nude mouse. Low magnification of a large tissue cell of this invention with a multilobed nucleus, prominent nucleoli and some condensation of chromatin along the nuclear membrane. The cytoplasm contains numerous granules of variable size and electron density, large Golgi complexes and numerous vesicles and tubular channels in the peripheral cytoplasm (×4950)
Figure 6:
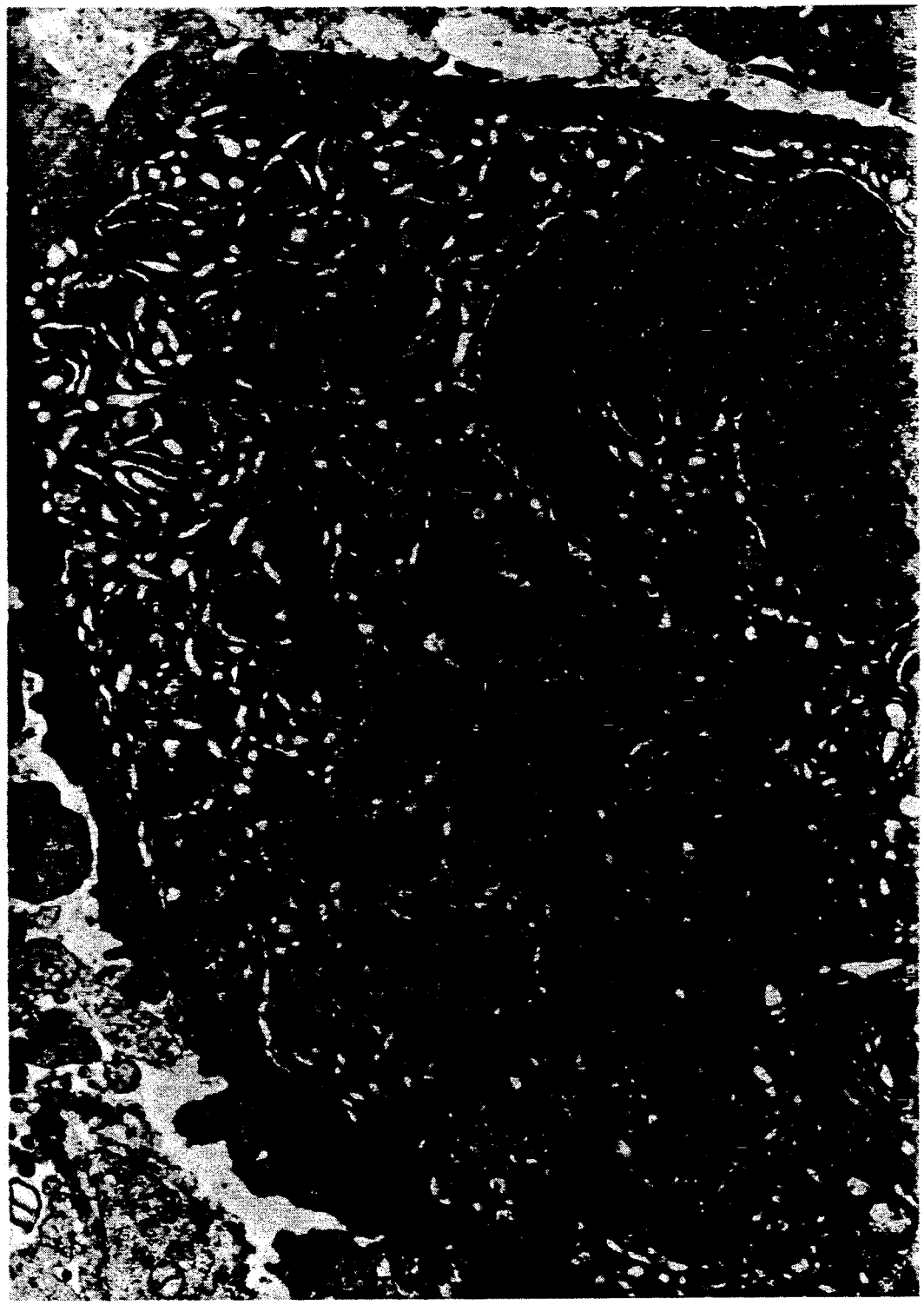
FIG. 6. Higher magnification of cells of this invention obtained from the nodular tissue removed from an athymic nude mouse showing a complex network of demarcation-like channels in the cytoplasm. Note the rim or organelle poor cytoplasm in the marginal zone (×10,800)
Figure 7A:
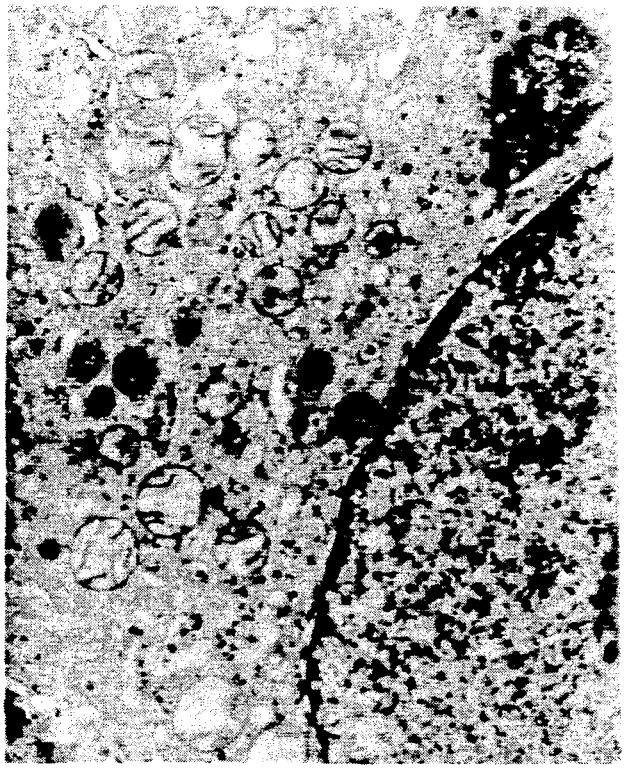
FIGS. 7a and 7b. Cells of this invention obtained from the nodular tissue removed from an athymic nude mouse containing numerous granules of variable size and electron density. The smaller granules contain a central electron dense core ("bull's eye") characteristic of alpha-granules (double arrow). Larger granules (single arrow) with more coarsely granular content and variable electron density are also present. (×15,000) B, bottom. Detail of larger granular in A showing granular matrix and central electron dense core (×25,000)
Figure 7B:
Figure 8:
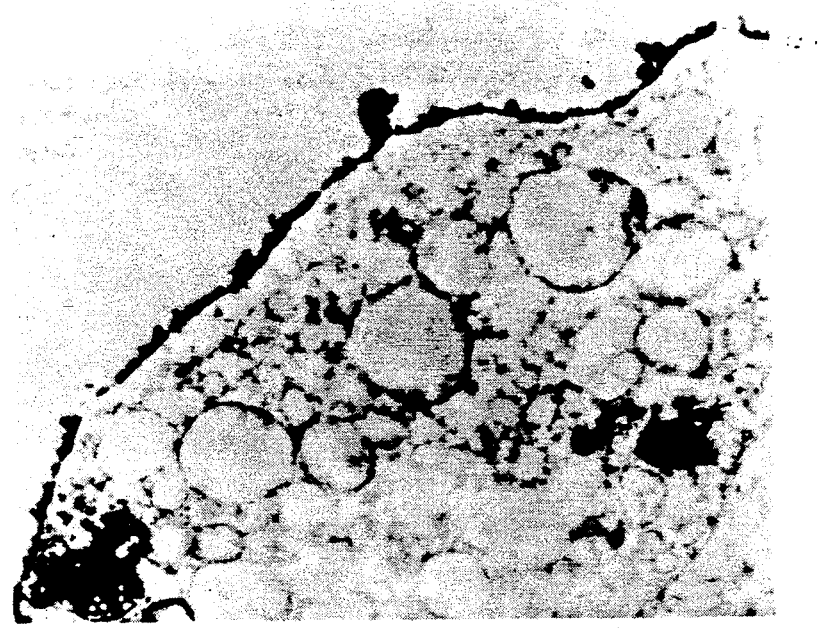
FIG. 8. Immunoelectronmicrograph of cells of this invention obtained from the nodular tissue removed from an athymic nude mouse labeled with anti-factor VIII antibody. A dense layer of peroxidase reaction product is seen on the cell membrane surface and in a large cytoplasmic granule corresponding to the larger granules in FIG. 7 (×20,000)

Ultrastructurally the cells of the nude mouse tumor (CHRF-288 xenograft) contain single convoluted or multilobed nuclei with prominent nucleoli and a thin rim of condensed nucleoprotein along the nuclear membrane as viewed in FIG. 5. The cytoplasmic margins were distinct with occasional interdigitating cell processes along the abutting surfaces of adjacent tumor cells. In the more poorly differentiated cells the cytoplasm was nondescript with numerous free ribosomes, polyribosomes, a small to moderate amount of rough endoplasmic reticulum (RER) and relatively sparse granules. The more differentiated cells had a complex division of the cytoplasm into three distinct zones. The first zone, a perinuclear zone, contained numerous ribosomes, profiles of RER, small and large granules, large Golgi apparatus, a few round to oval mitochondria with straight, thin tubular cristae and occasional centrioles. The second zone, an intermediate zone, contained numerous mitochondria, particulate glycogen, numerous polyribosomes and relatively frequent granules which varied in size and appearance. The cytoplasm in some cells was pervaded by a system of vessicles and tubules in the outer portion of this zone, suggestive of developing demarcation channels as shown in FIG. 6. The granules differed in size, shape, internal content and presence of a central dense nucleoid. Numerous small granules with an electron dense core surrounded by material of lesser density as depicted in FIG. 7 were present and appeared to bud from the Golgi apparatus. Larger membrane bound granules with either finely granular contents or more dense coarsely granular material were also present, some of which had a central dense core as observed in FIG. 8. And, a rim of condensed organelle poor cytoplasm formed the marginal third zone in the most differentiated cells, but no budding platelets were identified. Immunohistochemistry for localization of factor VIII antigen at the ultrastructural level showed dense labeling of the cell surface in addition to labelling of the larger cytoplasmic granules as can be seen in FIG. 8.

E. Products of CHRF-288 Xenograft

Tumors were grown in athymic nude mice, surgically removed, and then homogenized either in a neutral pH buffer (about 10 mM sodium phosphate, about 80 mM NaCl, about pH 7.4) or about 0.1N acetic acid. The resulting extract was then clarified by centrifugation and the pellet reextracted two times with about 1.0M NaCl (this is modeled after the procedure of Ross et al for the purification of PDGF, Raines, E. W. et al: *Methods in Enzymology*, 109:749–773, 1985. The combined supernatants were then dialyzed against a low salt (0.08M NaCl) buffer and the extract clarified by centrifugation. The growth factor activity found under acidic homogenization conditions was initially identified as PDGF by its ability to stimulate DNA synthesis in quiescent 3T3 cells, its stability at about 100° C., and its loss of activity, at about 100° C., in the presence of mercaptoethanol (Table 2). However, it is now believed that this growth factor activity is due to bFGF due to the Northern data analysis in Witte, D. P. et al: *J. Cell. Physiol.*, 137:86 (1988).

TABLE 2

| Sensitivity of Acid-Extracted Material to Mercaptoethanol | | |
| --- | --- | --- |
| Sample | | [³H]-dThd Incorporated (cpm) |
| Expt. I | Control | 4,352 |
| | +12.5 mcg extract | 20,946 |
| | +12.5 mcg(htd) | 23,019 |
| Expt. II | Control | 1,816 |
| | +18.75 mcg(dialyzed) | 19,261 |

TABLE 2-continued

| Sensitivity of Acid-Extracted Material to Mercaptoethanol | |
| --- | --- |
| Sample | [³H]-dThd Incorporated (cpm) |
| +18.75 mcg(htd, +MSH) | 6,968 |

A sample of acid extracted tumor (5 mg/ml) was diluted 1:20 in 10 mM Tris, 150 mM NaCl, pH 7.4 and heated at 100° C. for 5 minutes with or without 0.7% mercaptoethanol (MSH). Samples containing MSH were dialyzed against PBS before being used in the assay. Either 50 mcl (Expt. I) or 75 mcl of extract were tested in each experiment. Mitogenic activity was assayed as described herein. Briefly, serum-deprived 3T3 (Swiss) cells were stimulated by the addition of growth factor, and then 16–20 hours post addition the cells were pulsed with [³H]-thymidine (dThd). Data are expressed as trichloroacetic acid precipitable counts per minute.

Figure 9:
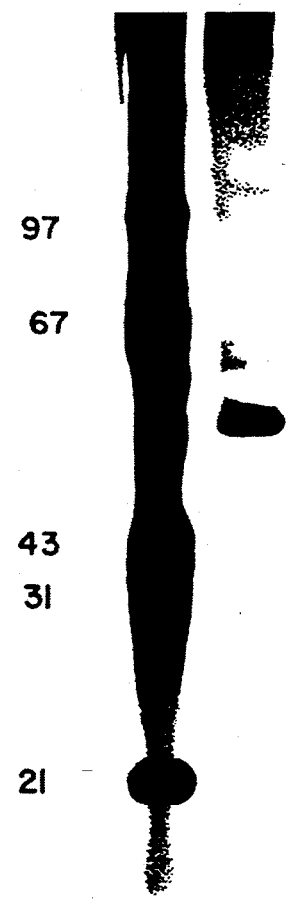
FIG. 9. Analysis of Affi-gel Blue purified basic fibroblast growth-like factor (bFGF) generated by cells of this invention obtained from the nodular tissue removed from an athymic nude mouse on a 10% SDS-PAGE gel. Approximately 2 micrograms of material were run on the gel (in the absence of mercaptoethanol) and the gel was then silver stained. The molecular weight standards are, from the top 97K, 67K, 43K, 31K and 21.5K. A major band is present at approximately 56K, and several other minor bands are present in the 30K region.

The material extracted at neutral pH has been further purified by binding to CM-Sephadex and growth factor activity was eluted, in batch technique, with 0.5M NaCl. Over 250,000 units (2 units of activity are equivalent to the mitogenic response of 5% calf serum) of growth factor activity were recovered at this step after starting with about 65 grams of tumor. The CM-Sephadex purified material has also been passed through an Affi-gel Blue column, and growth factor activity was eluted from the column with about 50% ethylene glycol, about 1.0M NaCl. This material appears to be similar to bFGF as it is heat and acid sensitive (Table 3), and will also down-regulate the EGF receptor (Table 4). bFGF is believed to down-regulate the EGF receptor which is also a property of PDGF, Bowen-Pope, D. F. et al: *J. Biol. Chem* 257:5161–5171 (1982); Nishimura, J., et al: *Proc. Natl. Acad. Sci. USA* 79:4303–4307 (1982). Heat inactivated extract did not down-regulate the receptor (Table 4). This material contains 1 unit of activity per 35 ng of protein (Table 5), and consists mainly of two major bands on a silver stained gel (FIG. 9). One of these bands is at about 56,000 Daltons; the others are in the range of about 30,000 Daltons. Co-incubation of the extract with ¹²⁵I-EGF, at about 4° C., did not inhibit EGF binding, nor was any cross-reacting material to an anti-EGF antibody found in the CHRF-288 xenograft extract. In addition, a 3T3 cell variant lacking EGF receptors responds to the extract, indicating that EGF is not the primary mitogen. This puts an upper limit on possible EGF contamination of the extract at about 0.1 ng/ml. This material also contains proteins which will cross-react, in an ELISA, with monoclonal antibodies directed against the amino terminal region of the v-sis peptide (obtained from the Scripps Institute) (Table 6). The above results suggest that v-sis-like peptides and a bFGF-like peptide is expressed by the CHRF-288 xenograft. Over 4,000 units of growth factor activity are believed to be present per gram of tumor, indicating that sufficient material is present for purification (15 grams of tumor can be obtained per mouse). To compare this to platelets, 3 units of out-dated platelets also contain about 4000 units of growth factor activity after the CM-Sephadex step, indicating that the CHRF-288 xenograft is truly an ample source for growth-like factor. The data presented in Table 5 indicates that after utilizing the Affi-gel Blue column, 1 unit of growth factor activity corresponds to 36 ng of material, and only a few protein bands are seen on an SDS-silver stained gel (FIG. 9).

TABLE 3
Heat And Acid Sensitivity Of Neutral pH Tumor Extract

| Sample | [³H] cpm Incorporated |
| --- | --- |
| Control | 22,865 |
| + extract | 222,196 |
| + heated extract | 19,211 |
| + acid-treated extract | 75,250 |

Tumor was extracted at neutral pH and purified through the Affi-gel Blue column. Approximately 4 units of activity (140 ng) were tested, in the presence of 1 mg/ml BSA. Heating consisted of placing the sample in a boiling water bath for 5 minutes. Acid treated samples were microdialyzed against 1.0M NH₄Ac, pH 3.5 and then left at pH 3.5 (4° C.) for 48 hours (shorter treatments reduce activity to a samller extent). The sample was then microdialyzed again to raise the pH to 7.4, and tested for mitogenic activity, as described in the legend to Table 2.

TABLE 4
Down-Regulation Of The EGF Receptor By The Megakaryocytic Extract

| Sample | % Control Binding |
| --- | --- |
| No addition | 100 |
| + crude PDGF | 63 |
| + tumor extract | 48 |
| + EGF | 52 |
| + heated tumor extract | 105 |

EGF binding was measured at a concentration of 5 ng/ml [¹²⁵I]-EGF for 4 hours at 4° C.. Non-specific binding was assayed in the presence of 500 ng/ml EGF, and was 10% of the total binding measured. Swiss 3T3 cells (at a density of 3 × 10⁴ cells/cm²) were preincubated with the samples to be tested for 2 hours at 37° C. prior to initiating the binding assay. All experiments were done in 35 mm dishes, and 4 units of crude PDGF were added (purified the Blue purified tumor extract (heated tumor was treated at 100° for 5 minutes) were tested, as was 1 ng/ml EGF. Control binding was 2624 cpm; the [¹²⁵I]-EGF had a specific activity of 30 mcCi/mcg. All points are the average of duplicate determinations, with a standard deviation of less than 7%.

TABLE 5
Purification of Growth Promoting Activity from the Tumor Line

| Sample | Total Units | Specific Activity (Units/mcg Protein) | Total Protein (mg) |
| --- | --- | --- | --- |
| Crude extract | 8.6 × 10⁵ | 0.11 | 7869 |
| CM-Sephadex (0.5M eluate) | 2.0 × 10⁵ | 2.63 | 76 |
| Affi-gel Blue eluate | 4.0 × 10⁵ | 27.8 | 14 |

Data are taken from a purification starting with 50 grams of tumor. Columns were run as described in the text. Note that running the Affi-gel Blue column results in an activation of mitogenic activity as compared to the CM-Sephadex eluate. Activities of fractions were determined by assaying various dilutions of fractions and determining the point at which 50% of the stimulation brought about 5% calf serum was reached. This point is defined as 1 unit of growth factor activity. All growth factor dilutions were done in DME/BSA (1 mg/ml).

TABLE 6
ELISA Results Using Anti-v-sis Monoclonal Antibodies

| Sample (antigen) | Monoclonal Antibody | Absorbance 410 nm |
| --- | --- | --- |
| SSV cell lysate | #1, 1/100 | .661 |
| | #2, 1/100 | .605 |
| Megakaryocyte extract | #1, 1/100 | .556 |
| | #1, 1/1000 | .387 |
| | #2, 1/100 | .790 |
| | #2, 1/1000 | .637 |

Antigen was prebound to a flexible 96 well plate for 18 hours at 4° C.. After washing appropriate dilutions of two monoclonal antibodies directed against the amino terminal end of the v-sis product (which is present in PDGF) were incubated with the dish, and then a second antibody, goat anti-mouse conjugated with beta-galactosidase, was added. beta-galactosidase activity was then assayed and the absorbance at 410 nm determined. Background levels of beta-galactosidase were also determined using BSA as the antigen, and those values (.230 for 1/100 dilution; .100 for a 1/1000 dilution) are subtracted from the values given above. The sample of megakaryocytic extract used was purified through the CM-Sephadex and Affi-gel Blue columns (1 unit is equivalent to 36 ng of material); and SSV-cell lysate was prepared by sonication (5 seconds) of SSV transformed 3T3 cells, which were obtained from the NIH.

Figure 10:
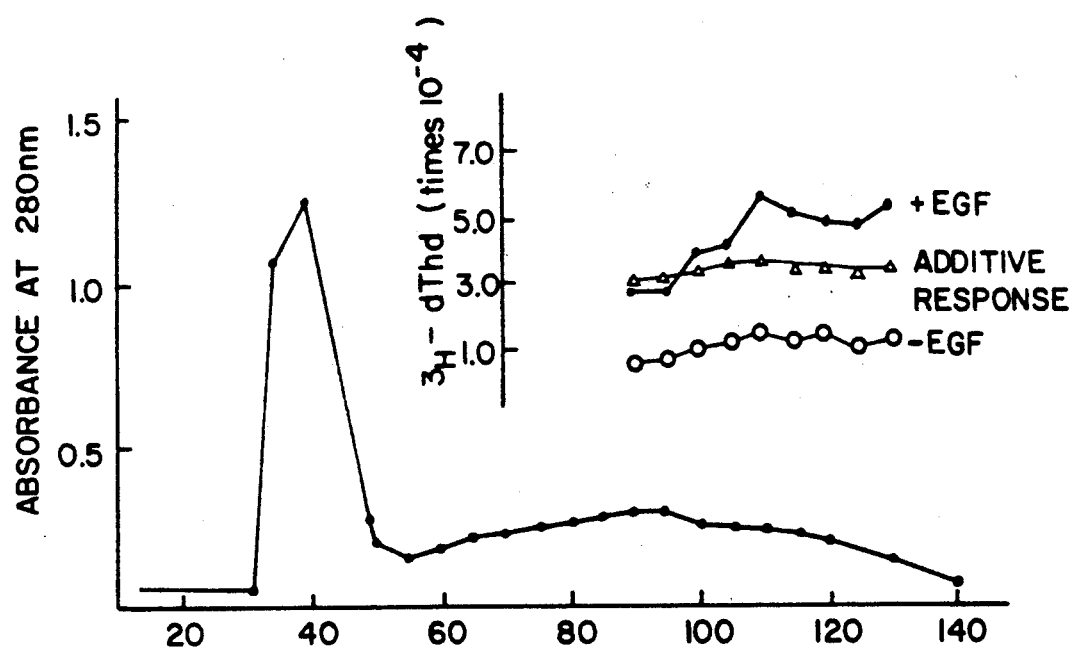
FIG. 10. P-60 chromatography of an acidic/ethanol extract of protein fractions derived from cells of this invention obtained from the nodular tissue removed from an athymic nude mouse which did not bind to CM-Sephadex. Material from 40 grams of tumor were treated as described herein and run through a 2.5×95 cm column of P-60 in 1.ON acetic acid. The column was run at 5 mls/h, and fractions of 3 ml were collected. Aliquots of various column fractions were then microdialyzed, in the presence of 100 micrograms BSA, against 4 mM HCl, and the resulting material then utilized for the following bioassays. The first was growth in soft agar in the presence of EGF and the positive fractions are indicated by the solid bar. The second assay was to determine if various fractions could synergistically enhance the mitogenic effect of EGF (2.5 ng/ml). The inset demonstrates the results and shows a clear enhancement of the additive response for fractions 110-140. EGF induced mitogenesis gave 37,000 cpm; background (no stimulation) was 11,000 cpm, and is subtracted from all values. For this experiment TGF-beta containing samples were preincubated with quiescent NRK cells for 8 hours before adding EGF and 10 microliters of each fraction was tested. DNA synthesis was then assayed 16-20 hours post EGF addition.

In addition to the growth-like factor activity, TGF-beta-like activity is believed to be found in the protein fraction which did not bind to the CM-Sephadex column (which is run at pH of about 7.4). These fractions were concentrated by Amicon ultrafiltration, dialyzed against about 1.0 N acetic acid, and lyophilized. The residue thus obtained was then extracted with an acidic ethanol solution and the supernatant fraction retained. Protein was then precipitated from these fractions by the addition of ethanol and ether, and the precipitate was redissolved in about 1.0 M acetic acid. Aliquots of this fraction would compete with EGF for binding to the EGF receptor (Table 7). Chromatography of the resulting extract in about 1.0N acetic acid on a P-60 column, allowed the demonstration of TGF-beta activity. TGF-beta activity can be shown by the following assays; fractions containing TGF-beta synergistically enhanced the EGF (2.5 ng/ml) induced mitogenesis of a rat fibroblast (NRK) cell line (FIG. 10); pre-incubation of the NRK cell line with the same column fractions reduced [¹²⁵I]-EGF binding to the high affinity EGF receptor; and finally, these same fractions also are believed to stimulate NRK cell growth in soft agar in the presence of EGF at 2.5 ng/ml. In addition, a crude extract for TGF-beta content (utilizing a radioreceptor assay) was assayed and cross-reactivity was shown at a level indicating that about 1 to about 2.5 micrograms of TGF-beta is present per gram of tumor.

TABLE 7
The Presence of TGF-Beta in The Megakaryocytic Extract

| Sample | [¹²⁵I]-EGF Bound, cpm/dish |
| --- | --- |
| Control | 2998 (100%) |
| + Extract | 2088 (70%) |

[¹²⁵I]-EGF (5 ng/ml) binding was assayed on confluent NRK cell monolayers as described in the legend to Table 4. Thirty mcg (20 mcl) of ether/ethanol precipitated extract was added to the cells simultaneously with the iodinated growth factor, and binding allowed to occur for 4 hours at 4° C.. Binding assays were done in triplicate with total binding at 3510 ± 82, non-specific binding at 511 ± 36, and in the presence of extract 2599 ± 180.

Figure 12:
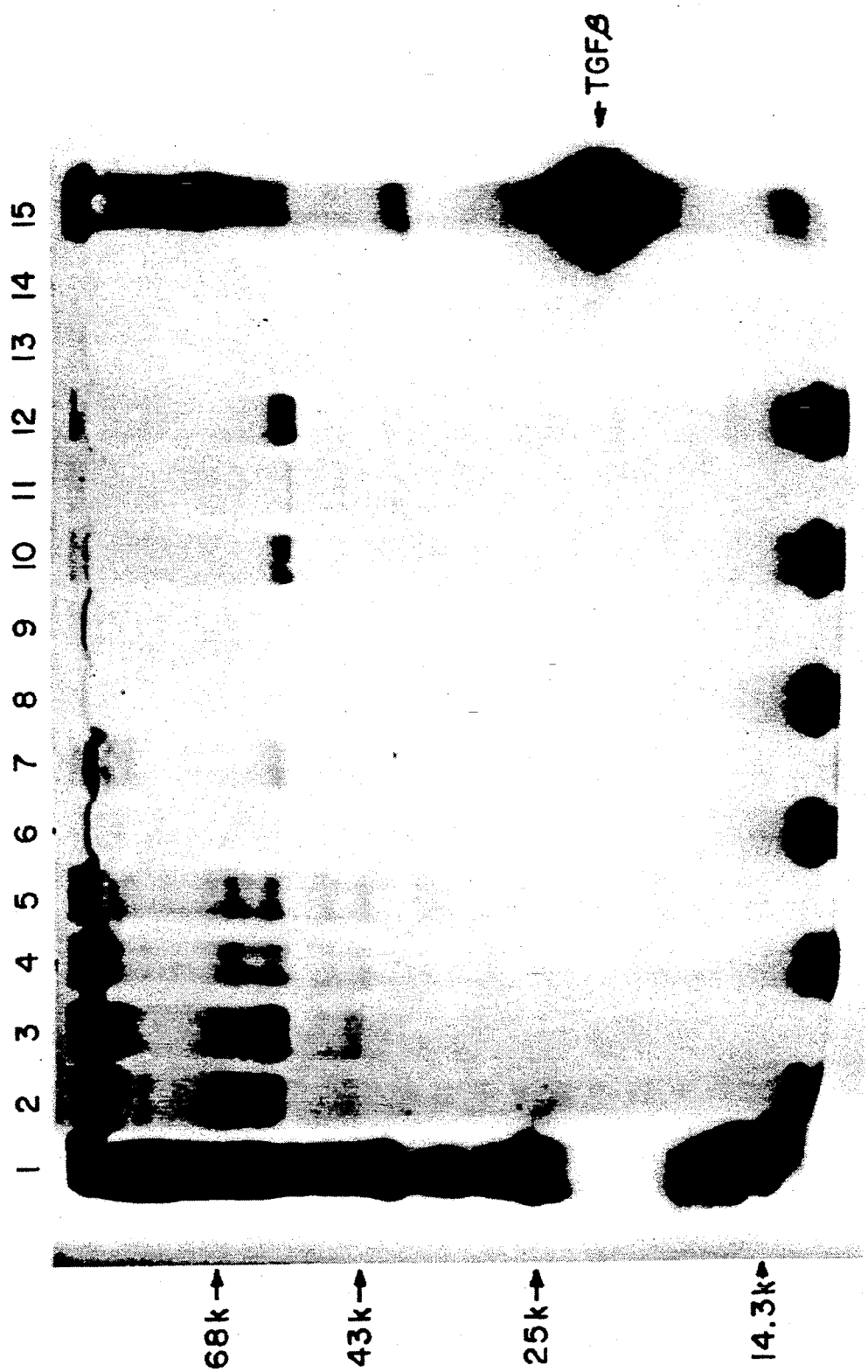
FIG. 12. An autoradiogram of immunoprecipitated, $[^{35}S]$-labeled tissue extracts of this invention obtained from the nodular tissue removed from an athymic nude mouse. Tumor nodules were excised from the mouse, dissociated into a suspension of singular cells using both trypsin and mechanical disruption. One million cells were plated per 35 mm dish in DME containing 10% the normal levels of methionine and cysteine and 2% dialyzed calf serum. After a one hour incubation at 37° 500 microcurie of $[^{35}S]$-methionine and 500 microcurie of $[^{35}S]$-cysteine were added to each dish, and the cells were harvested either after 3 or 24 hours of labeling. The following samples were utilized for the immunoprecipitations: the media bathing the cells, an acidic ethanol extract of sonicated cell pellets, and the detergent solubilized pellet from the non-soluble material in acidic ethanol. An equal number of TCA precipitable counts (50,000) was then utilized for all immunoprecipitation, using either anti-TGF-beta or normal rabbit serum. Immune complexes were pelleted using insoluble protein A and the complexes removed from the carrier by boiling in the presence of SDS. The samples were then run on 10% SDS-acrylamide gels, enhanced, dried, and exposed. This figure is a 10 day exposure at −80° C. Lanes 2 and 3 contain the media from cells harvested at 3 hours; lanes 4, 5 the 24 hour media; lanes 6, 7 the 3 hour acidic ethanol extract; lanes 8, 9 the 24 hour acidic ethanol extract; lanes 10, 11 the 3 hour detergent solubilized pellet; lanes 12, 13 the 24 hour solubilized pellet; and lane 15 $[^{125}I]$-TGF-beta. Even number lanes were immunoprecipitated with anti-TGF-beta, odd number lanes with normal rabbit serum.
Figure 11:
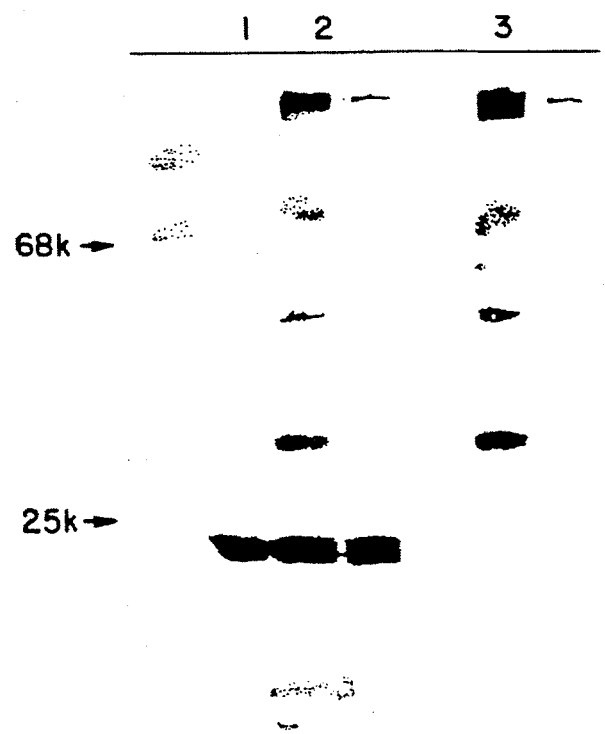
FIG. 11. Western blot analysis of an acidic ethanol extract of the megakaryocytic cell line of this invention obtained from the nodular tissue removed from an athymic nude mouse. Samples were run on 10% SDS-polyacrylamide gels and electroblotted to nitrocellulose. The nitrocellulose was blocked with BSA and incubated overnight with affinity purified antibodies to either TGF-beta or EGF. After washing, the membranes were incubated with gold-labeled goat anti-rabbit IgG and were then subjected to a silver enhancement procedure for intensifying the bands. The only major band which appears to be specific migrates with human platelet TGF-beta. Lanes 1 and 3 contain 10 ng platelet TGF-beta; Lanes 2 and 4 30 ng equivalents (based on inhibition of $[^{125}I]$-TGF-beta binding) of an acidic ethanol extract of the tumor line. Lanes 1-3 were treated with anti-TGF-beta; Lane 4, with anti-EGF. The anti-EGF antibody does not cross react with TGF-alpha.

Turning to FIG. 11, this figure shows a Western blot of an acidic ethanol extract of the megakaryocytic CHRF-288 xenograft of this invention obtained from a nodular tissue removed from an athymic mouse. As can be seen in FIG. 11, the major specific band visualized was at about 25,000 Daltons, running what is believed to be identical to platelet TGF-beta. The data in FIG. 12 is believed to demonstrate radiolabelling of the tumor line and immunoprecipitation of the TGF-beta precursors. After about a three hour labeling period with both [³⁵S]-methionine and [³⁵S]-cysteine, both about a 12,500 and about a 60–70,000 Dalton species are immunoprecipitated by the antibody to TGF-beta. In particular, the 60–70,000 Dalton species may not be soluble in acidic ethanol, as it is found primarily in the pellet following acidic ethanol treatment of the cells. These bands are not seen using normal rabbit serum. These may represent the monomer and precursor, respectively.

Since pulse-chase experiments may be utilized to study the biosynthesis of these growth-like factors, preliminary studies can be performed to determine if tumor cell suspensions will show significant protein labeling with [³⁵S]-methionine. A tumor nodule can be dissected from a mouse and minced in methionine-free Dulbecco's medium (supplemented with about 10% dialyzed calf serum) to which trypsin can be added to a final concentration of about 0.02%. The tumor fragments can then be further minced until a cell suspension is obtained and transferred to a centrifuge tube. After washing with medium, the cells can be transferred to 35 mm petri dishes. To each dish, at about $4.2 \times 10^5$ cells per milliliter, either 25, 50 or 100 microcurie of [$^{35}$S]-methionine can be added and incubated at about 37° C. for various time intervals. The [$^{35}$S]-methionine uptake can be determined from trichloracetic acid precipitate counts. After a slight lag, uptake is believed to be linear up to three hours after culturing the cells (Table 8) and proportional to the amount of [$^{35}$S]-methionine added to the media. Cells also are believed to remain viable for about 48 hours under these conditions (as determined by trypan blue exclusion).

It should be thus apparent to those skilled in the art, that this unique CHRF-288 xenograft of megakaryocytic lineage and origin, which can be cultivated continuously and in large quantities, contains growth-like factors having activities similar to those presently found in platelets. The growth-like factors generated by the CHRF-288 xenograft can be isolated and purified in accordance with techniques well known to those versed in this field and the techniques as set forth in copending application for U.S. patent having Ser. No. 06/884,714 and filed on Jul. 11, 1986.

TABLE 8

| Labeling Conditions | Time of Labeling (h) | cpm Incorporated/cell |
|---|---|---|
| [$^{35}$S]-met at 25 mcCi/ml | 1 | 0.35 |
| | 2 | 0.93 |
| | 3 | 1.87 |
| [$^{35}$S]-met at 50 mcCi/ml | 1 | 0.63 |
| | 2 | 1.80 |
| | 3 | 3.43 |
| [$^{35}$S]-met at 100 mcCi/ml | 1 | 1.10 |
| | 2 | 3.50 |
| | 3 | 7.67 |

[$^{35}$S]-Methionine Incorporation Into Dissociated Tissue Cells

Cells from a single tissue nodule were dissociated with trypsin and plated at $4.2 \times 10^5$ cells per 35 mm dish (1 ml/dish) in Dulbecco's modified Eagle's medium (methionine free) supplemented with 10% dialyzed calf serum and the indicated amount of labeled methionine. At the indicated times an aliquot of cells (200 mcl) was removed from the dish and trichloracetic acid precipitable counts determined.

EXAMPLE I

1. Extraction of the orbital Tissue

The infant patient was taken to the operating room at Children's Hospital Medical Center, Cincinnati, Ohio on Sep. 27, 1984, sterilely prepped and draped in the usual fashion. A left lower lid crease incision was marked off although a little lower than usual in order to center the incision over the tumor. The left lower lid was then infiltrated with about 2 mls of 1% Lidocaine 1:100,000 Epinephrine. After waiting for about 5 minutes, a skin incision was made, and sharp dissection was carried through the skin. Due to the excessive bleeding that was encountered, bovie cautery was utilized to go through the orbicularis to the orbital septum. Beneath the orbital septum, there was a bluish mass protruding. The orbital septum was then opened for the full width. A round domed mass with vertical striations that was bluish-red in color extending into the orbit was observed. A substantial quantity of this soft or extramedullary tissue was then excised using first scissors and then Takahasi cup forceps.

After the tumor biopsy had been completed, the left orbit was much softer. While there was no bleeding from the wound edges, the tumor itself continued to bleed not quickly, but in a rather sustained fashion. Electrocautery, thrombin and gelfoam were utilized, but the bleeding persisted. Since the bleeding was somewhat extensive, it was believed to be inappropriate to close the wound. The wound was therefore packed open with iodiform gauze dressing. This slowed the bleeding substantially. Several sterile eye patches were then applied, and the infant patient was awakened and taken from the operating room in satisfactory condition.

The soft or extramedullary tissue mass, that was removed from the left orbit, was taken fresh and sterilely from surgery to pathology for implantation in an athymic nude mouse.

2. Implantation of the Orbital Tissue

With respect to the implanation of the soft tissue extracted from the left orbit of the infant patient, an athymic nude mouse derived from NIH stock of Swiss background was first anesthetized lightly with an effective dose of methoxyfluorane under sterile conditions in a laminar flow hood. An adequate portion of an orbital tissue sample obtained from the surgically removed orbital mass was intimately mixed with sterile minimum essential medium (MEM). Thereafter, the tissue sample was delicately minced into about 1 mm sections. A thirteen (13) gauge trocar needle assembly was introduced subcutaneously under the skin of one of the flanks of the anesthetized nude mouse. After insertion, the stylus was removed from the trocar syringe assembly. Approximately 0.5 ml of the intimately mixed mixture containing the minced tissue sections was injected subcutaneously into the flank via the inserted trocus. Following the injection of the intimately mixed mixture into the flank, the stylus was reinserted into the trocus to introduce any mixture remaining in the trocus into the flank of the nude mouse. Approximately 0.5 mls of the intimately mixed mixture containing the minced tissue sections was also injected subcutaneously under the skin into the other flank of the anesthetized nude mouse repeating the above described procedure.

Approximately ten weeks following the implantation, the nude mouse was carefully sacrificed, and the tumor tissue that was cultivated in each flank was surgically harvested utilizing standard surgical laboratory techniques. The cells grew as a solid nodule in the subcutaneous tissue of each flank, measuring approximately 3.0 cm in greatest dimension. An adequate portion of the surgically removed tumor tissue was successfully passaged in other athymic nude mice derived from NIH stock of Swiss background by repeating the above described procedure. Once the cell line was adapted to the athymic nude mice, the interval between passages for the tumor cell line of this invention has been found to be approximately four weeks. All athymic nude mice were maintained in filter topped cages.

EXAMPLE II

While the cells of the CHRF-288 xenograft grow well within the nude mouse as a solid tumor, such growth precludes the use of the CHRF-288 xenograft for many valuable experiments. In order to adapt the cells of the CHRF-288 xenograft to in vitro growth, the marrow microenviroment is mimicked as closely as possible, by using an in vitro system of adherent stromal cells obtained from long term human bone marrow cultures for use as a feeder layer.

Two procedures have been developed to enable human bone marrow mononuclear cells (BMMC) to be salvaged from unused fractions of T-cell depletion procedures, as set forth in Reisner, Y. et al: *Lancet*, 2:327 (1981), which is incorporated herein by reference in its entirety. BMMCs are salvaged by repeating the gelatin red cell sedimentation step on the initial red cell sediment obtained, as indicated in Reisner, Y. et al: *Lancet*, 2:327 (1981). The reclaimed BMMCs are concentrated and washed twice with PBS, 2% human serum albumin (HSA, Travenol Laboratories), 1% penicillin/streptomycin and resuspended at a final cell concentration of $5 \times 10^7$ cells/ml. BMMCs are also reclaimed from the soy bean lectin agglutinate fraction of the T-Cell depletion procedure by disaggregating the cells with 0.2M galactose in PBS, washing the separated cells two time with Media 199, 1% penicillin/streptomycin, and resuspending them to a final cell concentration of $5 \times 10^7$ cells/ml. The cultures of stromal layers derived from the lectin agglutinate fraction will not give rise to hematopoietic cells since the stem cell population is removed; however, the stromal cell layers that are obtained from this population of cells are equally effective as a feeder layer as are the cells salvaged from the red cell sediment. Both types of stromal cell populations are used, although they have not been mixed together prior to initiating the stromal cultures. LTBM cultures are established by plating $3-5 \times 10^7$ BMMCs in 25 cm² tissue culture flasks (Corning) with 10 ml of LTBM media, consisting of Fischer's complete media for leukemic cells, 25% horse serum, and 1% penicillin/streptomycin. Initially 1 mcM hydrocortisone is added to the media and cells are incubated in a 37°, 100% humidified incubator with 5% $CO_2$ in air. After 5 or 6 days, all non-adherent cells (which would contain hematopoietic stem cells) are removed, the adherent cells are washed with media, and fresh LTBM media is added. Cultures are then fed weekly by removal of all media and replacement with fresh LTBM media. Hydrocortisone is removed from the culture media after 4 weeks of culture, and always prior to a culture's use as a feeder layer. From these cultures, stromal layers are developed which consist of fibroblasts, adipocytes, and macrophages, as is evident in FIG. 13A. The removal of non-adherent cells from the cultures is important to select against long-term development of hematopoietic cells.

The two above-described LTBM cultures are inoculated with a cell suspension derived from the CHRF-288 xenograft. Cells from the CHRF-288 xenograft rapidly attach to the LTBM feeder layer and proliferate, forming large colonies of tumor cells which are attached to the adherent stromal cells (FIGS. 13B, 13C, and 13D). Cell growth is vigorous and a nearly confluent monolayer of tumor cells is developed over the stromal layer. The doubling time of the cells is about 67 hours when grown on the stromal layer (data not shown). Cultures are fed weekly by complete replacement of LTBM media with fresh media. Once confluent, tumor cells (CHRF-288 xenograft) are shed into the medium, and can be replated on new LTBM cultures without any cessation of cell proliferation.

CHRF-288 cells are weaned from the stromal layer over a period of four months. Cells which are spontaneously released from the stromal layer are collected and plated into a new dish in the absence of stromal cells. Some stromal cells are carried over by this procedure, however, and attach to the flask and proliferate. However, many of the CHRF-288 cells remain unattached to the stromal cells, and the process of replating is repeated. This is continued until no further stromal cells are being carried over, and the CHRF-288 cells have obtained the capacity to grow in the absence of such cells, providing that the initial seeding density is high (about $10^5$ cells/flask). At low densities, cell proliferation does not occur. Thus, the cells of the CHRF-288 xenograft have been cloned by performing the procedure (limiting dilution) on LTBM cultures on which adherent stromal cells developed.

Fourteen independent clones designated as CHRF-288-1 to CHRF-288-14 are isolated, removed from the stromal layer, and grown in tissue culture. One clone, clone 11, designated as CHRF-288-11, is examined as discussed hereinbelow. The cells of the cloned CHRF-288-11 cell line are passaged in the absence of feeder layers by biweekly feeding in Fishers medium supplemented with either horse or bovine calf serum. The cells of the other thirteen cloned cell lines, designated as CHRF-288-1 to CHRF-288-10 and CHRF-288-12 to CHRF-288-14, are also passaged in the absence of feeder layers by biweekly feeding in Fishers medium supplemented with either horse or bovine calf serum.

1. Microscopy

In situ photomicrographs of unstained viable cultures are taken on a Zeiss inverted stage microscope using Hoffman modulation optics. Cytocentrifuge preparations of the cultured tumor cells derived from the CHRF-288 xenograft are stained with Wright's stain on an Ames Hema-Tek slide stainer (Miles) followed by a manual 5 minute Giemsa stain for routine light microscopic analysis. Cells for routine electron microscopy are fixed in about 3% glutaraldehyde in 0.175M cacodylate buffer and post-fixed in about 1% osmic acid prior to embedding in LX112. Uranyl acetate stained sections are examined with a Phillips 400 transmission electron microscope. Tumor cells are processed for the platelet peroxidase reaction as previously described in Breton-Gorius, J. et al: *Blood*, 51:45 (1978), which is incorporated herein by reference in its entirety. Negative controls for the platelet peroxidase reaction are processed in an identical manner except that hydrogen peroxide is omitted from the reaction mixture.

2. Flow cytometry

Monoclonal antibodies are obtained from Ortho diagnostics (OKT series), Becton/Dickson (Leu series and IL2-R and CALLA) and from Coulter Immunology (MY7, MY9). CHRF-288-11 cells used for flow cytometry are grown in Fischers medium containing 25% horse serum, washed twice with PBS, 2% horse serum, pH 7.4, incubated with fluorescein labeled mouse monoclonal antibodies at $5 \times 10^6$ cells/ml for 30 minutes at 4° C. with occasional shaking, and washed twice in PBS prior to analysis. Cells labeled by indirect methods are processed as described above, washed twice in PBS, 2% horse serum, incubated 30 minutes on ice with fluorescein labeled goat anti-mouse IgG with occasional shaking, and washed twice with PBS prior to analysis. The antibody incubations are all performed between concentrations of 0.5 to 25 mcg/ml. Approximately ten thousand cells are counted per determination. The DNA content of the cells is measured using an EPICS flow cytometer equipped with digitalizing equipment. Cells for DNA analysis are prepared as described in Clevenger, C. V. et al: *Cytometry*, 6:208 (1985), which is incorporated herein by reference in its entirety, except that prior to analysis the labelled cell suspension is filtered through an 88 mcm nylon mesh filter to remove any agglutinated cells.

3. Immuncytochemistry

CHRF-288-11 cells are incubated in serum-free media for 24 hours to allow serum factors to dissociate from the cells, and then cytocentrifuged on poly-L-lysine coated glass slides for immunohistochemistry. The slides are air dried and rinsed in three changes of PBS buffer containing 1% BSA. The antibodies are obtained from Accurate Chemical and Scientific Co. (anti-Factor VIII antigen), Dr. Shirley Levine (University of Texas, San Antonio, Tex.) (anti-platelet factor IV [PF4]), Dr. William Dean (University of Louisville, Louisville, Ky.) (anti-human platelet Ca++-ATPase), Dr. Ronald Jensen (University of California, Lawrence Livermore Laboratories, Calif.) (anti glycophorin A), Dr. Rodger McEver (University of Oklahoma, Okla. Medical Research Foundation, Oklahoma City, Oklahoma) (anti-platelet glycoprotein IIbIIIa complex), and the DAKO Corporation for antibodies against myeloperoxidase. Non-immune rabbit and mouse sera are used as negative controls. Immunofluorescent stained slides are analyzed with a Zeiss epifluorescence microscope. Results obtained using cells pre-incubated in serum-free media for 24 hours are the same as those obtained using cells without serum-free pre-incubation, and the results are similar if the cells are grown in either horse or calf serum.

4. Karyotype Analysis

Karyotype analysis of the growing cells is performed using standard procedures which have been described previously in Wang, Wuu, S. et al: *Cancer Research*, 48:983 (1988), which is incorporated herein by reference in its entirety.

5. Western Analysis

Western analysis for the presence of glycophorin A is carried out as described in Rearden, A. et al: *Mol. Immunol.*, 22:369 (1985), which is incorporated herein by reference in its entirety, using monoclonal antibody 10F7 at a dilution of 1:200.

6. Growth Factor Analysis

For the determination of growth factor activity in CHRF-288-11 cell extracts, the cells are extracted in either a neutral buffer ($1 \times 10^6$ cells in 1.0 ml of 20 mM Tris, 0.25M Sucrose, 1 mM EDTA, 0.1 mM PMSF, pH 7.0) or in an acidic buffer ($4.8 \times 10^6$ cells in acidic ethanol as disclosed in Assoian, R. et al: *J. Biol. Chem.*, 258:7155 (1983), which is incorporated herein by reference in its entirety). Neutral homogenates are clarified by centrifugation and aliquots are added directly to serum-depleted 3T3-NR6 cells as previously described in Witte, D. P. et al: *J. Cell. Physiol.*, 137:86 (1988), which is incorporated herein by reference in its entirety. Measurement of analysis of the [$^3$H]-thymidine incorporation into DNA is performed as described in Witte, D. P. et al: *J. Cell. Physiol.*, 137:86 (1988). Acidic ethanol extracts are concentrated by ether precipitation, as described in Assoian, R. et al: *J. Biol. Chem.*, 258:7155 (1983), and dissolution of the pellet in 200 microliters 4 mM HCl. Aliquots of this extract are added to high density, exponentially growing A549 cells as described in Witte, D. P. et al: *J. Cell. Physiol.*, 137:86 (1988), and the extent of inhibition of DNA synthesis is determined.

7. RNA Analysis

The methods for the procedures are described below. Total RNA is isolated from $1 \times 10^8$ cells (or 1 gram of CHRF-288 solid tumor tissue, Witte D. P. et al: *J. Cell. Physiol.*, 137:86 (1988)) as described previously in Chomczynski, P. et al: *Anal. Biochem.*, 162:156–159 (1987), which is incorporated herein by reference in its entirety. For Northern analysis, the total RNA is passed through an oligo-dT column to purify polyA+-RNA. Northern analysis of TGF-beta 1 mRNA is performed according to a modification of the previously described procedure in Maniates, T. et al: *In Molecular Cloning, A Laboratory Manual*, Cold Spring Harbor Laboratory, Cold Spring Harbor, N.Y., p. 202 (1982), which is incorporated herein by reference in its entirety. After electrophoresis, RNA is transferred to nitrocellulose and prehybridized for about 4 hours at about 42° in $20 \times SSC$ ($1 \times SSC$ contains 0.15M NaCl, 0.015M sodium citrate), about 50 mM sodium phosphate, $2 \times$ Denhardt's solution, about 0.1% sodium dodecyl sulfate (SDS), and about 50% formamide. The TGF-beta 1 probe (pBas, Genentech, Derynck, R. et al: *Nature*, 316:701–705 (1985) which is incorporated herein by reference in its entirety) with [$^{32}$P]-labeled cDNA probe, at $1 \times 10^6$ cpm/ml, is carried out for about 16 h at about 42° in $4 \times SSC$, 40 mM sodium phosphate, $2 \times$ Denhardt's solution, 0.1% SDS, and about 40% formamide. After hybridization, filters are washed four times at room temperature in $2 \times SSC$ containing 0.2% SDS for 5 minutes and again for 20 minutes. Subsequent washes are two times in $0.2 \times SSC$ containing 0.2% SDS at about 50° and once in $0.1 \times SSC$ containing 0.1% SDS at about 55°. The filter is then exposed to Kodak XAR film at about −70° with an intensifying screen for 15 hours before development.

Quantitation of bFGF mRNA is done by solution hybridization. A vector is constructed which contains the 474 bp human bFGF insert from the plasmid mp18+bFGF, which is provided by Synergen, Boulder Co. The insert is excised as an XbaI-HindIII fragment and inserted into a similarly cut pBluescript SK+ transcription vector (Stratagene Cloning Systems, Inc., La Jolla, Calif.). RNA transcripts are generated from vectors linearized at each end of the insert and purified from agarose gels. Antisense probes are made per manufacturers recommendations except that alpha-[$^{32}$P]-CTP is used exclusively at a final CTP concentration of about 20 mcM (50 mcCi/0.4 nmole). Unlabeled sense strand RNA, used as internal quantitation standards, are made in large quantity, purified by agarose gels, and quantitated spectrophotometrically. Hybridization and quantitation are performed as previously described in Aronow, B. et al: *Genes Dev.*, 3:1384 (1989), which is incorporated herein by reference in its entirety, except that they are performed at about 53° for about 15 h in approximately 15 ml of buffer containing 400,000 cpm of antisense probe, 30 mg of either cellular RNA or carrier tRNA, and for standard quantitation, 0–200 pg of sense-strand RNA. Unhybridized RNA is digested by addition of 185 microliters of an ice-cold solution that contains 0.45M NaCl, 0.1M LiCl, 10 mM Tris HCl, pH 7.4, 1 mM EDTA and 4 mcg/ml RNase A. The solution is then incubated at about 16° for approximately 30 minutes, processed without denaturation, and electrophoresed on a 3.8% polyacrylamide gel that contains $1 \times TBE$. See Maniates, T. et al referenced hereinbefore. Autoradiography of the gel is for about 24 hours at approximately −70° C.

8. Characteristics Of The Cloned CHRF-288-11 Cell

Once the CHRF-288-11 cells are established in tissue culture, it is demonstrated that they still retain the megakaryocytic features observed in the CHRF-288 xenograft. This is accomplished in a variety of ways. Karyotype analysis of the cloned cells (50, XY, +6q−, +8, +17, +21, 12p+, −10, +19p+, −15, 1p+, 6p−, exhibited by 10 out of 13 cells examined) demonstrate that the cells of the CHRF-288-11 cell line exhibit similar chromosomal markers as described for the CHRF-288 xenograft. The karyotype demonstrates trisomy for chromosomes 6, 8, 17, 19, and 21. The extra chromosome 6 has a large deletion and trisomy for chromosome 19 is variable although greater than 90% of the megakaryocytic cells of the CHRF-288-11 cell line carry this alteration. The only differences between the cloned cells of the CHRF-288-11 cell line and the cells of the original CHRF-288 xenograft as grown in nude mice are a small 6p deletion (p23), and the loss of one chromosome 10. Thus, the cells of the CHRF-288-11 cell line retain significant features of the karyotype even after long term in vitro culturing, and suggests that the cells of the CHRF-288-11 cell line are similar to the cells of the CHRF-288 xenograft passaged in nude mice.

While the 10 out of the 13 cells of the CHRF-288-11 cell line that were examined exhibit the above indicated karyotype, two of the thirteen cells examined exhibit a karyotype of 49XY and one of the thirteen cells examined exhibit a karyotype of 48XY. Notwithstanding these difference in chromosome number, the changes in the chromosomes for these three cells were consistent with the changes in the chromosmoes for the other 10 cells examined, excepting trisomy characteristics. In view of the results obtained concerning the karyotype of the cells of the CHRF-288-11 cell line, it is believed that the correct karyotype for such cells is 50XY and, moreover, that the karyotype is constant.

Figure 14:
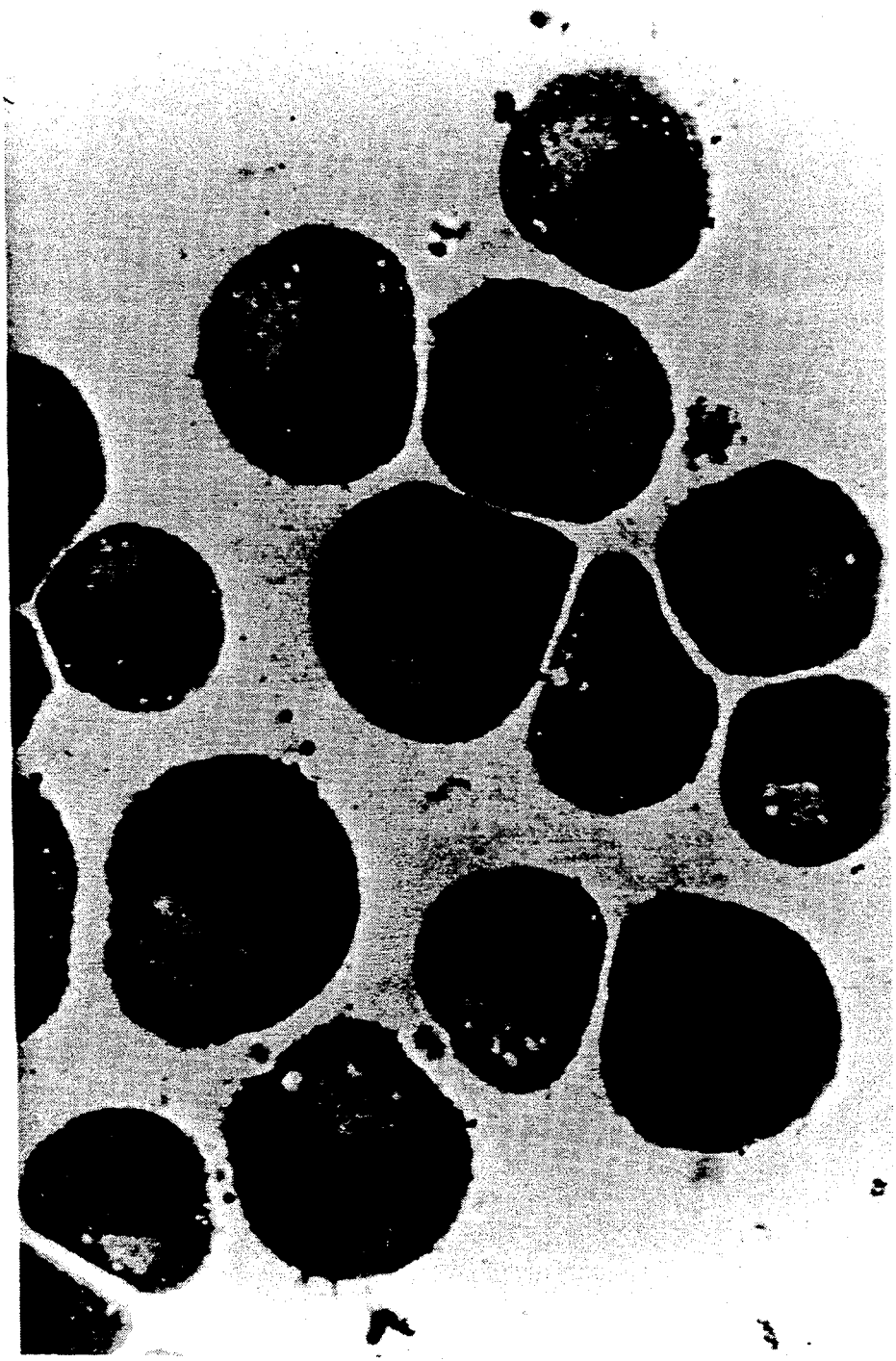
FIG. 14. Wright's-Giemsa stained cytocentrifuge preparations of CHRF-288-11 cells. Most of the cells have a single round nucleus with one to three prominent nucleoli. The cells have a large amount of slightly granular basophilic staining cytoplasm at the periphery that surrounds a prominent eosinophilic staining perinuclear Golgi zone. Many of the CHRF-288-11 cells show cytoplasmic protrusions on the surface. One large CHRF-288-11 cell has three nuclear lobes arranged around a prominent Golgi zone. (Wright's-Giemsa, Magnification= ×680)
Figure 16A:
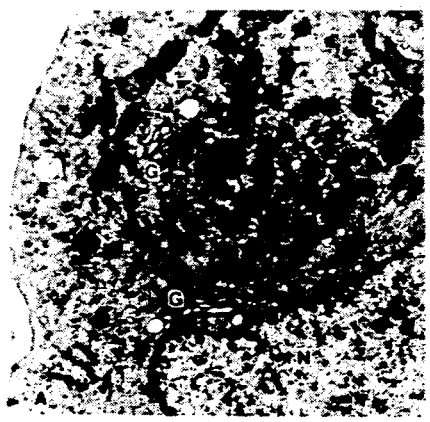
FIG. 16. Electron photomicrographs of CHRF-288-11 culture cells. Panel A shows an eccentric nucleus (N) and cytoplasm containing numerous mitochondria, polyribosomes, prominent Golgi apparatus (G) and numerous empty vesicles and small granules with a dense central matrix (arrowhead). Panel B shows a higher magnification of a cell containing larger granules (300–600 nm). These granules (arrowheads) have a diffuse granular matrix with a dense nucleoid resembling alpha-granules. Panel C shows a CHRF-288-11 cell with numerous small round granules (100–300 nm) that contain an electron dense matrix surrounded by a clear halo. One of these dense granules can be seen arising from a Golgi complex (arrowhead). FIG. D illustrates the platelet peroxidase reaction. There is an intense perinuclear reaction (N-nucleus) as well as in the endoplasmic reticulum. The Golgi cisternae granules contained no reactivity (Magnification; A—×12,000, B—17,000, C—13,100, D—×13,100)
Figure 16B:
Figure 16C:
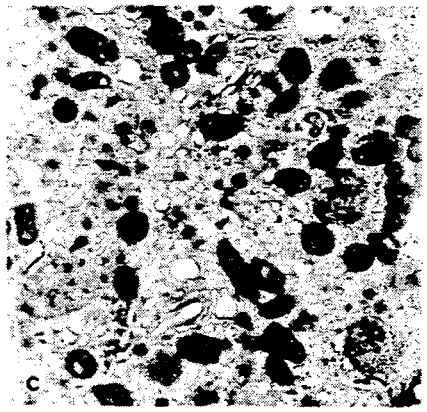
Figure 16D:

It is also determined, both microscopically and immunologically, that the megakaryocyte specific genes which are expressed by the cells of the CHRF-288 xenograft are also expressed by the cells of the CHRF-288-11 cell line, i.e., the cells are phenotypically unchanged. Light microscopic analysis of Wright-Giemsa stained cells (FIG. 14) demonstrate that the cells of the CHRF-288-11 cell line range in size from about 15-20 microns in diameter, and contain a highly basophilic, slightly granular cytoplasm with a prominent eosinophilic perinuclear Golgi zone. Most of the cells of the CHRF-288-11 cell line have a single oval or round nucleus with one to three prominent nucleoli. Some cells of the CHRF-288-11 cell line having bilobed nuclei are occasionally present (2–3% of the total) and a few CHRF-288-11 cells have complex multilobed nuclei (less than 0.5% of the population). Several CHRF-288-11 cells with cytoplasmic protrusions are also observed, although the majority of CHRF-288-11 cells are rounded. Immunohistochemistry demonstrates the presence of platelet glycoprotein IIbIIIa protein complex and factor VIII protein, which are characteristic of both platelets and megakaryocytes (FIGS. 15A, 15B). Greater than about 95% of the CHRF-288-11 cells express gpIIbIIIa protein complex, while about 30–40% of the population express Factor VIII protein. The factor VIII positive CHRF-288-11 cells are generally the larger, more mature cells, but there are also immature cells present that show little cytologic evidence of maturation. Immunohistochemistry on acetone permeabilized CHRF-288-11 cells identify a diffuse staining for platelet factor IV (PF4) in the cytoplasm (FIG. 15C), as well as platelet Ca++-ATPase immunoreactivity (FIG. 15D). In contrast to the Factor VIII stain, PF4 is generally expressed in most CHRF-288-11 cells, although there are more cell to cell variability in intensity, and the PF4 signal is focally concentrated in many of the CHRF-288-11 cells. Myeloperoxidase immunoreactivity is not detected (not shown). Electron microscopy (FIGS. 16A, 16B, 16C, and 16D) shows most of the CHRF-288-11 cells have a single nucleus with a single prominent nucleolus and the chromatin is moderately condensed. Most of the CHRF-288-11 cells contain few cytoplasmic organelles other than large numbers of polyribosomes. The more mature CHRF-288-11 cells (FIG. 16A) generally have extensive rough endoplasmic reticulum, frequent mitochondria, and well developed Golgi complexes associated with numerous small vesicle, some of which are coated. There are also numerous granules that vary in size and electron density. Small round granules (100–300 nm) are evident, and contain an electron dense matrix that either completely fills the granule or is surrounded by a clear halo in the more differentiated cells. These granules generally are seen budding near the Golgi complex but occasionally are seen to arise from areas of the endoplasmic reticulum in the periphery of the CHRF-288-11 cells (FIG. 16C). Ultrastructural features of the smaller dense granules resemble the various stages of platelet dense granule formation as described by White, J.: *Am. J. Path.*, 53:791 (1968), which is incorporated herein by reference in its entirety. Larger granules (about 300–600 nm), resembling alpha-granules, have a diffuse finely granular matrix and occasionally a moderately dense nucleoid (FIG. 16B). The platelet peroxidase reaction (FIG. 16D), as analyzed by electron microscopy, is positive in greater than about 80% of the CHRF-288-11 cells. The reaction product is localized to the perinuclear zone and in the endoplasmic reticulum.

Cloned CHRF-288-11 cells are also examined by flow cytometric analysis for the expression of cell surface markers characteristic of T-cells, B-cells, natural killer cells, lymphoblastic leukemia, monocytes, and megakaryocytes. As can be seen in Table 9, the CHRF-288-11 cells express the HLA-Dr backbone antigen, gpIIbIIIa protein complex, and epitopes recognized by MY7 (CD13) and MY9 (CD33) monoclonal antibodies. No T- or B-cell markers are evident on the CHRF-288-11 cells, nor is there evidence for the expression of glycophorin A by Western blot analysis (FIG. 17) and immunocytochemistry (data not shown), or hemoglobin as determined by immunocytochemistry (not shown). Benzidine staining also fails to reveal the presence of heme (data not shown). These data indicate that the CHRF-288-11 cell line is expressing megakaryocytic markers, and that it is not biphenotypic for the erythroid lineage.

Figures 17, 18A, 18B:
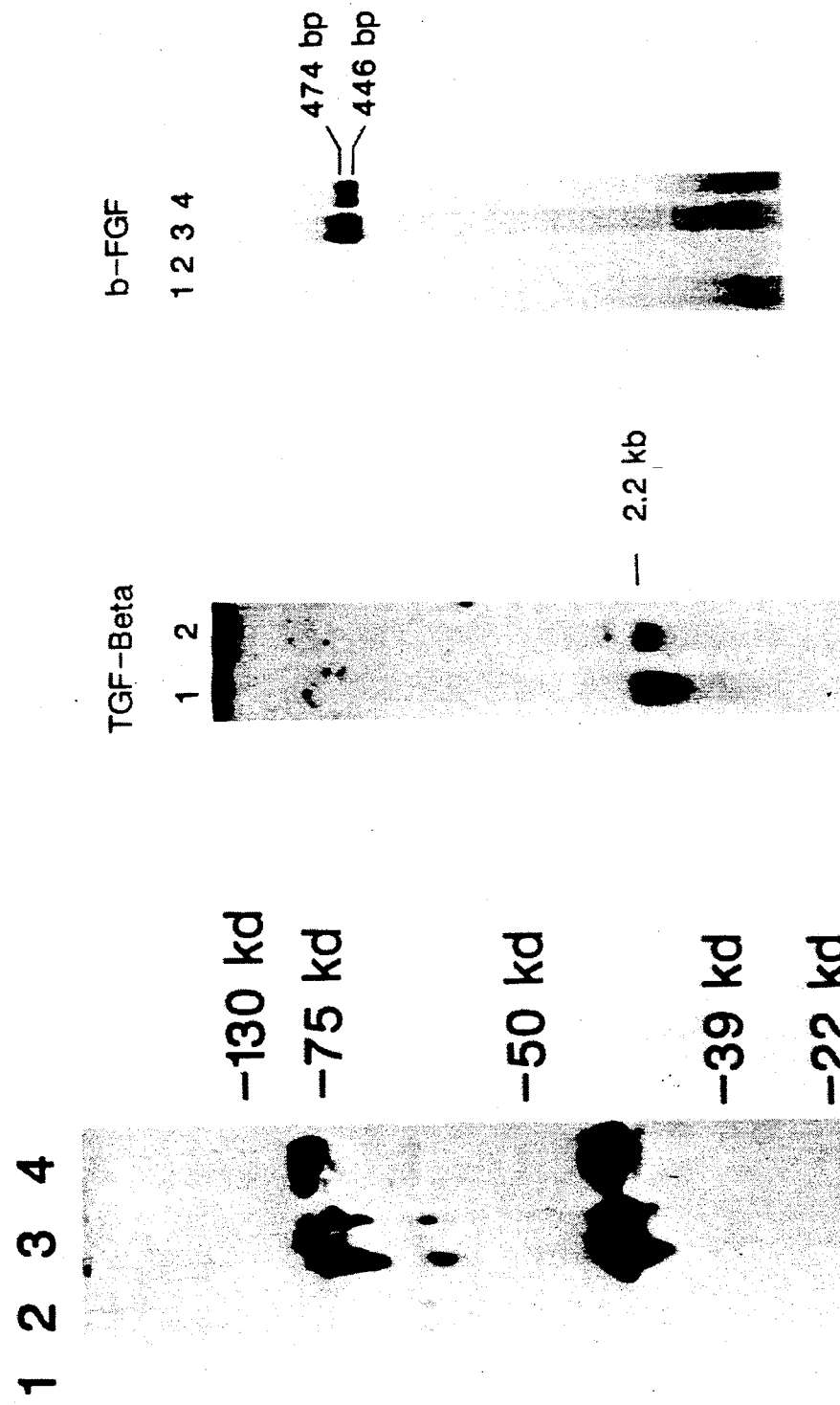
FIG. 17. Western blot analysis of CHRF-288-11 and erythrocyte membrane ghosts for glycophorin A. Conditions were as described in Bigbee, W. L. et al: *Mol. Immunol.*, 20:1353 (1983), which is incorporated herein by reference in its entirety. Erythrocyte ghosts were prepared as previously described in Whittenberger, B. et al: *Proc. Natl. Acad. Sci. USA*, 75:5457 (1978). Lanes 1 and 2 are solubilized CHRF-288-11 cells (50 and 25 micrograms, respectively) whereas lanes 3 and 4 are solubilized erythrocyte ghosts (50 and 25 micrograms, respectively). No immunoreactivity is seen with the CHRF-288-11 cells.
FIGS. 18A and 18B. Molecular analysis of CHRF-288-11 RNA. The results in FIG. 18A demonstrate a Northern blot analysis using the TGF-beta 1 probe. Total RNA was extracted from $10^8$ CHRF-288-11 cells and 1 gram of CHRF-288 xenograft tissue as described in Witte, D. P. et al: *J. Cell. Physiol.*, 137:86 (1988), which is incorporated herein by reference in its entirety, and run over a poly-dT column to isolate poly A+-RNA. Five micrograms of poly A+-RNA were run per lane through an agarose-formaldehyde gel and transferred to nitrocellulose as described in the text. The blot was then probed with the insert of a TGF-beta1 containing plasmid. The probe hybridizes to a unique 2.2 kb band as previously described in Witte, D. P. et al: *J. Cell. Physiol.*, 137:86 (1988) for both the cultured cells (lane 1) and the CHRF-288 xenograft (land 2), indicating the presence of TGF-beta mRNA. The results in FIG. 18B demonstrated the quantitative determination of bFGF mRNA present in the CHRF-288-11 cell line. Radiolabeled RNAs anti-sense to the 474 bp coding portion of bFGF mRNA was hybridized in solution to total RNA, digested with RNAse A, and then electrophoresed on non-denaturing 3.8% polyacrylamide gels. To quantify the RNAs, parallel hybridizations were also performed with spectrophotometrically determined quantities of sense-strand bFGF mRNA prepared from transcription vectors (not shown). Each lane was loaded with the hybridization products of 30 micrograms of the total RNA. Full-length bFGF mRNA protected fragments 474 and 446 bases long in equal abundance, utilizing RNA isolated from either CHRF-288-11 cells (lane 3) or CHRF-288 xenograft from nude mice (lane 4). The autoradiograph shown was exposed for about 36 hours at about $-70°$ C. without intensifying screens. RNA from a mesoblastic nephroma (lane 1), and an osteogenic sarcoma (lane 2) show no signal.
Figure 19A:
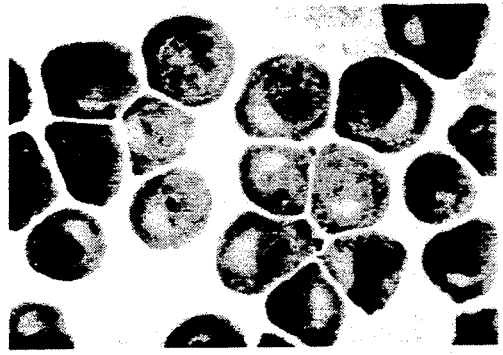
FIGS. 19a, 19b, 19c, 19d, 19e, and 19f, changes after PMA treatment of CHRF-288-11 cells. Panels A-D represent Wright's stained cytocentrifuge preparations of CHRF-288-11 cells before and after treatment with about $10^{-8}$M PMA: Panel A, untreated controls; Panel B, 2 days after PMA treatment; Panel C, 4 days after PMA treatment; and Panel D, 6 days after PMA treatment. All fields are at the same magnification, 1000×. Panels E and F demonstrate flow cytometric DNA analysis of untreated, control CHRF-288-11 cells (E), and CHRF-288-11 cells treated with about $10^{-8}$M PMA for 4 days (F). S1, S2, and S3 refer to cells in intermediate states of DNA synthesis between 2N and 4N, 4N and 8N, and above 8N, respectively. The mean fluorescent intensities of the 2N, 4N, and 8N peaks are 48.3, 96.5, and 190.0, respectively. Approximately 50,000 cells were counted for each analysis.
Figure 19B:
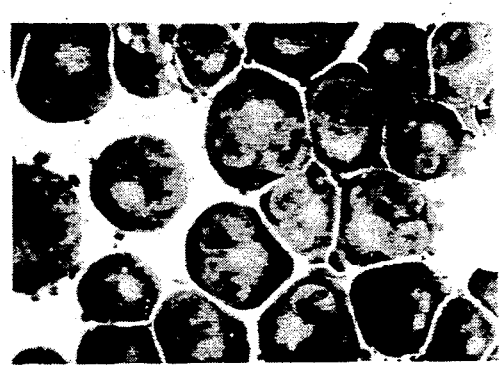
Figure 19C:
Figure 19D:
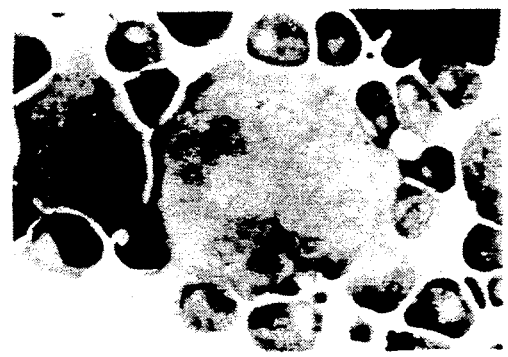
Figure 19E:
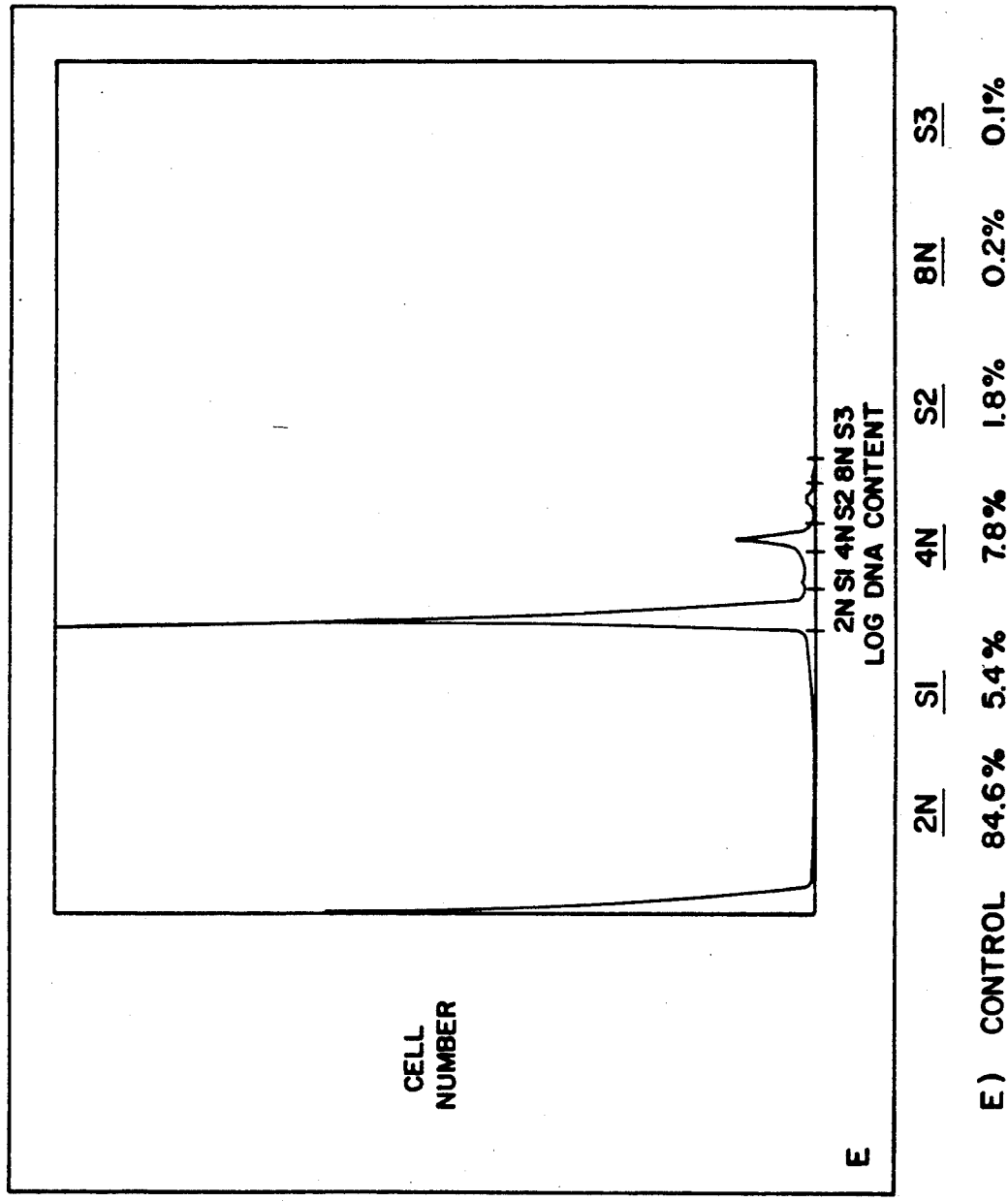
Figure 19F:
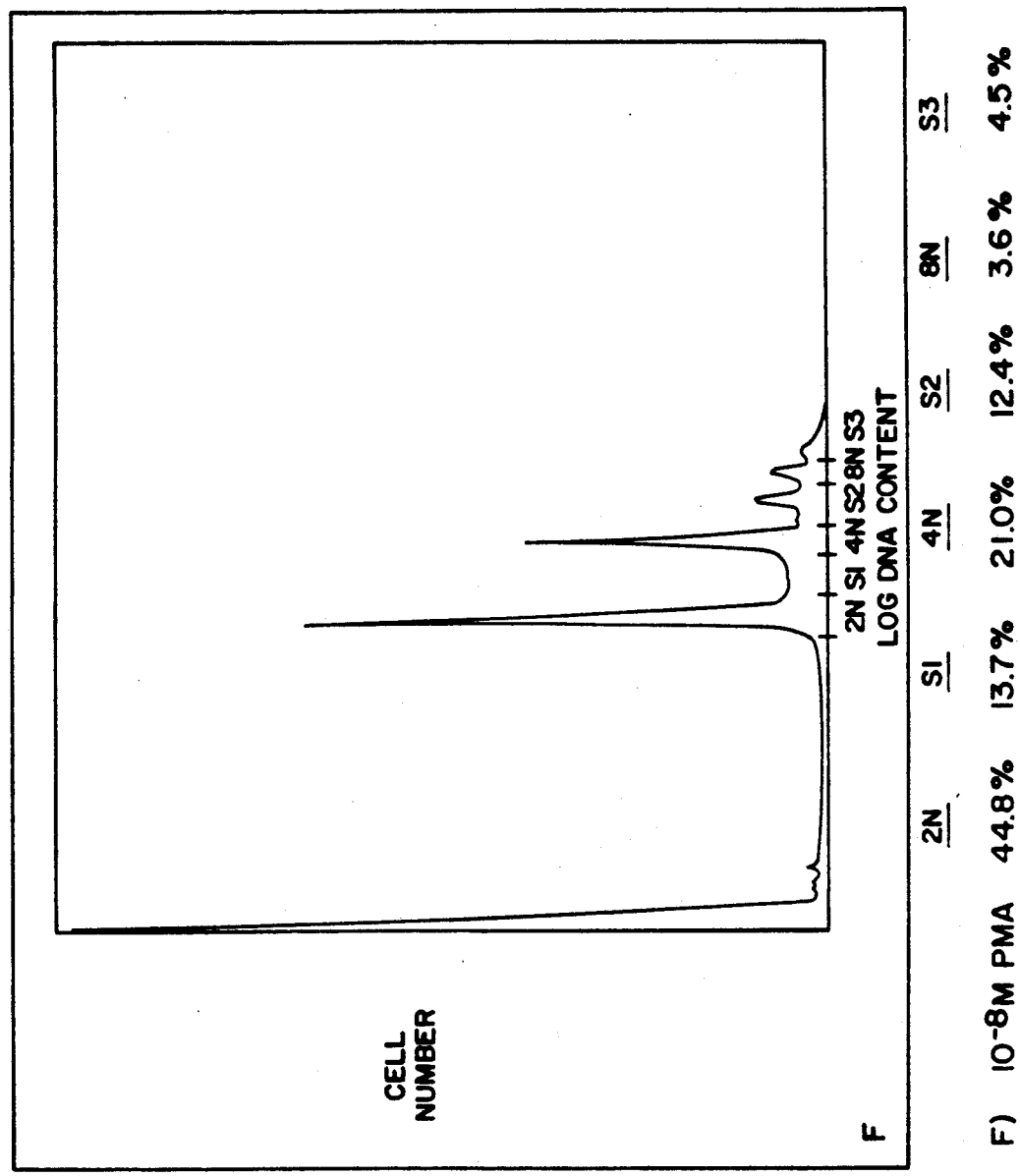

Cloned CHRF-288-11 cells are also examined for the production of basic fibroblast growth factor (bFGF) and transforming growth factor-beta (TGF-beta), two factors which are synthesized in large quantity by the cells of the CHRF-288 xenograft from which the cells of the CHRF-288-11 cell line are derived. Northern blot analysis of the RNA from the cultured CHRF-288-11 cells (FIG. 18A) using a probe specific for TGF-beta 1 show a strong hybridization signal at 2.2 kb, identical to the signal in the megakaryocyte solid tumor RNA. This indicates that CHRF-288-11 cells express TGF-beta 1 message, and the data in Table 10 indicate that a TGF-beta 1 activity is also present in CHRF-288-11 cell extracts. Solution hybridization analysis of total RNA prepared from the cultured CHRF-288-11 cells for bFGF transcripts indicates the presence of such transcripts (FIG. 18B). Full length bFGF mRNA protect a fragment 474 bases long, as well as a fragment 446 bases long in equal abundance. The 474 base band corresponds to the size of the control sense strand signal which does not show any other bands (data not shown). This is believed to indicate that the 446 base band results from cellular processing of the mRNA. The quantities of each species is determined based upon densitometric comparison to the results of hybridization to synthesized sense strand RNA from the same riboprobe vector as described in Aronow, B et al: *Genes Dev.*, 3:1384 (1989). The cultured CHRF-288-11 cells contain approximately 5 pg of the 474 base species per 30 micrograms total RNA, and 6.8 pg (per 30 micrograms of total RNA) of the 446 base species. Similarly, the cells of the CHRF-288 xenograft contain about 3.4 pg of the 474 base species and 4.6 pg of the 446 base species, both per 30 mcg of total RNA. Total RNA from a mesoblastic nephroma, which produces aFGF but not bFGF, as described in Witte, D. P. et al: *Lab. Invest.*, 60:353 (1989) which is incorporated herein by reference in its entirety, and total RNA from an osteogenic sarcoma, which does not produce bFGF, gives no signal in these assays indicating less than 0.03 pg per 30 micrograms total RNA based on the signal intensity of the control sense strand (FIG. 18B). These data, coupled with the biological activity demonstrated in Table 11, indicate that cells of the CHRF-288-11 cell line are producing active forms of bFGF, as previously shown in the cells of the CHRF-288 xenograft.

9. PMA Treatment of CHRF-288-11 Cells

Treatment of CHRF-288-11 cells with $10^{-8}$M PMA induces morphological and DNA ploidy changes similar to megakaryocytic differentiation, as can be seen in FIG. 19. Untreated control cells (FIG. 19A) demonstrates a homogenous population with about 97.5% of the CHRF-288-11 cells in a mononuclear state, about 2.0% binucleated, and about 0.5% appearing to have four nuclear lobes. Within two days of PMA induction, greater than about 50% of the CHRF-288-11 cells increase in size and about 29–30% appear to contain two nuclei (FIG. 19B). After four days of PMA treatment, the percentage of binucleated cells of the CHRF-288-11 cell line remain approximately the same, however about 6% of the CHRF-288-11 cells have about 4 to 8 nuclear lobes (FIG. 19C). After 6 days of PMA treatment, the percentage of responding CHRF-288-11 cells is the same as day 4, however occasional CHRF-288-11 cells with up to about 16 nuclear lobes are evident (FIG. 19D). Flow cytometric analysis using propidium iodide labelling suggests that these morphological changes represent increases in the ploidy values of the treated cells. Untreated CHRF-288-11 cells demonstrate a fairly normal DNA cell cycle pattern (FIG. 19E) with about 84.6% of the CHRF-288-11 cells in the 2N ($B_0/G_1$) peak, about 5.4% in S phase ($S_1$), and about 7.8% in a 4N peak ($G_2/M$). There appears to be a secondary S phase ($S_2$) containing about 1.8% of the CHRF-288-11 cells, which likely corresponds to the about 2% binucleated cells observed morphologically. After 4 days of PMA treatment, the 2N peak decreases by about 40%, whereas the $S_1$ phase and 4N cells increase to about 13.7% and about 21%, respectively (FIG. 19F). This is believed to occur even though the cellular proliferation rate decreases by about 60% (data not shown). In addition, about 8.1% of the treated CHRF-288-11 cells contain an 8N or greater DNA content ($8N + S_3$).

TABLE 9

Immunocytochemical Characteristics of Cells of the CHRF-288-11 Cell Line

| Antibody | Antigen Cluster Designation | Specificity | % Reactivity |
|---|---|---|---|
| Leu1 | CD-5 | T-cell | 0.0(−) |
| OKT3 | CD-3 | T-cell | 0.7(−) |
| OKT11 | CD-2 | T-cell | 0.8(−) |
| Leu2A | CD-8 | T-Cytotoxic/Suppressor | 0.4(−) |
| OKT8 | CD-8 | T-Cytotoxic/Suppressor | 0.0(−) |
| Leu3A | CD-4 | T-Helper/Inducer | 2.0(−) |
| OKT4 | CD-4 | T-Helper/Inducer | 1.0(−) |
| OKT6 | CD-1b | Thymocyte | 0.5(−) |
| Leu7 | — | NK-cell | 0.0(−) |
| Leu9 | CD-7 | NK-cell | 0.3(−) |
| Leu12 | CD-19 | B-cell | 0.5(−) |
| Leu16 | CD-20 | B-cell | 0.2(−) |
| IL-2R | CD-25 | Interleukin-2 Receptor | 0.4(−) |
| CALLA | CD-10 | Common Acute Lymphoblastic Leukemia Antigen | 0.4(−) |
| OKM5 | CD-36 | Monocytes, Platelets | 0.4(−) |
| OKDR | — | HLA-Dr Backbone Antigen | 86.4(+) |
| T10 | $CD_{w}$-41 | Platelet Glycoprotein IIbIIIa | 99.7(+) |
| Tab | $CD_{w}$-41 | Platelet Glycoprotein IIbIIIa | 98.7(+) |
| MY7 | CD-13 | Early myeloid cells, monocytes | 90.9(+) |
| MY9 | CD-38 | Early myeloid cells, monocytes | 95.7(+) |

Flow cytometric analysis of cultured CHRF-288-11 cells. Analyses is performed on an Ortho Spectrum III analytical flow cytometer and labeling is performed as described in Methods. CHRF-288 cells are positive for HLA-Dr antigen, and gpIIbIIIa protein complex, and epitopes for monoclonal antibodies MY7 and MY9 are also present on the CHRF-288-11 cells. This profile indicates CHRF-288-11 cells are committed to the megakaryocytic lineage.

TABLE 10

Growth factor activity in Cells of the CHRF-288-11 Cell Line

| Cell Extract Neutral extraction: | Growth Factor Activity Units of mitogenic activity: |
|---|---|
| 0.7 mcl | 0.22 |
| 3.4 mcl | 1.02 |
| 17.2 mcl | 2.31 |

| Acidic-ethanol extraction: | Percent of inhibition of A-549 cell DNA synthesis: |
|---|---|
| 0.75 mcl | 19.6 |
| 1.25 mcl | 23.7 |
| 2.50 mcl | 34.3 |
| TGF-beta1 (1 ng/ml) | 30.8 |

Cells of the CHRF-288-11 cell lines are extracted in accordance with well know techniques. From these data, the CHRF-288-11 cells contain about 59 units of mitogenic activity per $10^6$ cells, and approximately 8.5 ng of TGF-beta equivalents per $10^6$ cells.

The present invention may, of course, be carried out in other specific ways than those herein set forth without departing from the spirit and essential characteristics of the invention. For instance, the continuous CHRF-288 xenograft of the present invention is described as being cultivated in athymic nude mice. Nonetheless, it should be appreciated by those versed in the art that the continuous CHRF-288 xenograft may be cultivated in other suitable athymic nude animals, such as athymic nude guinea pigs and athymic nude rabbits. Likewise, it should be appreciated that other feeder layers may be used as culture mediums suitable for propagating in vitro cell lines derived from solid tumors or cells of megakaryocytic lineage and origin. Also, it may be desirable to alternate cell growth between cell culture medium and mice for the generation of hormone producing cells. The present embodiments are, therefore, to be considered in all respects as illustrative and not restrictive and any changes coming within the meaning and equivalency range of the appended claims are to be embraced therein.

Having described our invention, we claim:

1. A continuous human in vitro cell line derived from cells designated ATCC CRL 9139 comprising monophenotypic cells of megakaryoctic lineage and having a constant karyotype of 50 XY having characteristics similar to colony forming unit megakaryoblasts, and approximately 80% of said cells have the ability to express platelet peroxidase, said cells further having at least one of the following characteristics:
   a. granulated cytoplasm, said granules being characteristic for alpha-granules;
   b. expresses gpIIbIIIa;
   c. expresses Factor VIII; and
   d. platelet Factor IV.

2. A human in vitro cell line of claim 1, said cells having a diameter in the range of between about 15-20 microns.

3. A human in vitro cell line of claim 1, said cells being derived from human extramedullary tissue.

4. A human in vitro cell line of claim 1, certain of said cells having the ability to express at least one protein selected from the group consisting of basic fibroblast growth factor, transforming growth factor-beta and beta-thromboglobulin.

5. A human in vitro cell line of claim 1, certain of said cells being morphologically and cytochemically similar to at least colony forming unit megakaryoblasts of the megakaryocytic series.

6. A human in vitro cell line of claim 1, wherein said cells undergo further differentiation to a more mature form when exposed to a phorbol ester.

7. A human in vitro cell line of claim 1, wherein said cells have the ability to express at least one protein selected from the group consisting of gpIIbIIIa protein complex, GMP-140, platelet $Ca^{++}ATPase$, CD13, CD33, CD38, OKT9 and HLA-DR.

8. A human in vitro cell line of claim 1, certain of said cells having the ability to express at least one mRNA encoding a protein selected from the group consisting of PDGF-A chain, bFGF, TGF-beta and TGF-alpha.

9. A human in vitro cell line as deposited with the American Type Culture Collection (ATCC) under accession no. CRL 10107.

* * * * *